United States Patent
Haffner et al.

(10) Patent No.: US 9,636,255 B2
(45) Date of Patent: May 2, 2017

(54) UVEOSCLERAL DRUG DELIVERY IMPLANT AND METHODS FOR IMPLANTING THE SAME

(75) Inventors: David Haffner, Mission Viejo, CA (US); Kenneth Curry, Oceanside, CA (US)

(73) Assignee: DOSE MEDICAL CORPORATION, San Clemente, CA (US)

( * ) Notice: Subject to any disclaimer, the term of this patent is extended or adjusted under 35 U.S.C. 154(b) by 1036 days.

(21) Appl. No.: 13/201,423

(22) PCT Filed: Feb. 12, 2010

(86) PCT No.: PCT/US2010/024128
§ 371 (c)(1),
(2), (4) Date: Mar. 2, 2012

(87) PCT Pub. No.: WO2010/093945
PCT Pub. Date: Aug. 19, 2010

(65) Prior Publication Data
US 2012/0165933 A1    Jun. 28, 2012

Related U.S. Application Data

(60) Provisional application No. 61/152,651, filed on Feb. 13, 2009.

(51) Int. Cl.
*A61F 2/14*    (2006.01)
*A61F 9/007*    (2006.01)
(Continued)

(52) U.S. Cl.
CPC ........ *A61F 9/00781* (2013.01); *A61F 9/0017* (2013.01); *A61K 31/00* (2013.01);
(Continued)

(58) Field of Classification Search
CPC ........ A61M 2210/0612; A61L 2430/16; A61F 9/00781; A61F 9/0017
See application file for complete search history.

(56) References Cited

U.S. PATENT DOCUMENTS

| | | |
|---|---|---|
| 4,521,210 A | 6/1985 | Wong |
| 4,846,793 A | 7/1989 | Leonard et al. |

(Continued)

FOREIGN PATENT DOCUMENTS

| | | |
|---|---|---|
| CN | 101396335 A | 4/2009 |
| WO | WO 01/80825 A2 | 11/2001 |

(Continued)

OTHER PUBLICATIONS

International Search Report and Written Opinion in PCT/US2011/061967 mailed Jun. 28, 2012. (In 4 Parts due to size of file—Part 1 of 4—Part 2 of 4—Part 3 of 4—and Part 4 of 4).

(Continued)

*Primary Examiner* — Laura Bouchelle
*Assistant Examiner* — Anh Bui
(74) *Attorney, Agent, or Firm* — Knobbe, Martens, Olson & Bear, LLP

(57) ABSTRACT

Devices and methods for treating intraocular pressure are disclosed. The devices include drug delivery implants for treating ocular tissue. Optionally, the devices also include shunts for draining aqueous humor from the anterior chamber to the uveoscleral outflow pathway, including the supraciliary space and the suprachoroidal space. The drug delivery implants can be implanted in ab interno or ab externo procedures.

23 Claims, 15 Drawing Sheets

(51) Int. Cl.

| | | |
|---|---|---|
| *A61F 9/00* | (2006.01) | |
| *A61K 31/00* | (2006.01) | |
| *A61L 27/18* | (2006.01) | |
| *A61L 27/54* | (2006.01) | |
| *A61M 27/00* | (2006.01) | |
| *A61M 37/00* | (2006.01) | |
| *A61M 25/00* | (2006.01) | |
| *A61M 25/01* | (2006.01) | |
| *A61M 25/02* | (2006.01) | |

(52) U.S. Cl.
CPC ............. *A61L 27/18* (2013.01); *A61L 27/54* (2013.01); *A61M 27/00* (2013.01); *A61M 37/00* (2013.01); *A61L 2300/604* (2013.01); *A61L 2430/16* (2013.01); *A61M 25/00* (2013.01); *A61M 25/0105* (2013.01); *A61M 2025/0286* (2013.01); *A61M 2210/0612* (2013.01)

(56) References Cited

U.S. PATENT DOCUMENTS

| | | | |
|---|---|---|---|
| 4,853,224 A | 8/1989 | Wong | |
| 4,863,457 A | 9/1989 | Lee | |
| 4,997,652 A | 3/1991 | Wong | |
| 5,164,188 A | 11/1992 | Wong | |
| 5,378,474 A | 1/1995 | Morella et al. | |
| 5,378,475 A | 1/1995 | Smith et al. | |
| 5,443,505 A | 8/1995 | Wong et al. | |
| 5,502,052 A | 3/1996 | DeSantis | |
| 5,516,522 A | 5/1996 | Peyman et al. | |
| 5,629,008 A | 5/1997 | Lee | |
| 5,766,242 A | 6/1998 | Wong et al. | |
| 5,773,019 A | 6/1998 | Ashton et al. | |
| 5,824,072 A | 10/1998 | Wong | |
| 5,869,079 A | 2/1999 | Wong et al. | |
| 5,902,598 A | 5/1999 | Chen et al. | |
| 6,007,511 A | 12/1999 | Prywes | |
| 6,063,116 A | 5/2000 | Kelleher | |
| 6,063,396 A | 5/2000 | Kelleher | |
| 6,217,895 B1 | 4/2001 | Guo et al. | |
| 6,331,313 B1 | 12/2001 | Wong et al. | |
| 6,375,972 B1 | 4/2002 | Guo et al. | |
| 6,506,411 B2 | 1/2003 | Hunter et al. | |
| 6,548,078 B2 | 4/2003 | Guo et al. | |
| 6,726,918 B1 | 4/2004 | Wong et al. | |
| 6,764,698 B1 | 7/2004 | Byun et al. | |
| 6,998,137 B2 | 2/2006 | Shih et al. | |
| 7,083,802 B2 | 8/2006 | Peyman | |
| 7,445,793 B2 | 11/2008 | Niwa et al. | |
| 7,458,953 B2 | 12/2008 | Peyman | |
| 7,585,517 B2 | 9/2009 | Cooper et al. | |
| 7,815,592 B2 | 10/2010 | Coroneo | |
| 8,062,657 B2 | 11/2011 | Edelman et al. | |
| 8,071,120 B2 | 12/2011 | Wong | |
| 8,404,269 B2 | 3/2013 | Snyder et al. | |
| 8,425,929 B2 | 4/2013 | Huang et al. | |
| 8,440,216 B2 | 5/2013 | Huang et al. | |
| 8,444,589 B2 | 5/2013 | Silvestrini | |
| 8,454,582 B2 | 6/2013 | Dejuan et al. | |
| 2002/0013572 A1 | 1/2002 | Berlin | |
| 2002/0102307 A1 | 8/2002 | Guo et al. | |
| 2004/0115268 A1 | 6/2004 | Ashton et al. | |
| 2004/0127843 A1 | 7/2004 | Tu et al. | |
| 2004/0176341 A1 | 9/2004 | Chou et al. | |
| 2004/0180075 A1 | 9/2004 | Robinson et al. | |
| 2005/0008673 A1 | 1/2005 | Snyder et al. | |
| 2005/0119737 A1* | 6/2005 | Bene | A61F 9/00781 623/4.1 |
| 2005/0175708 A1 | 8/2005 | Carrasquillo et al. | |
| 2005/0232972 A1 | 10/2005 | Odrich | |
| 2005/0244461 A1 | 11/2005 | Nivaggioli et al. | |
| 2005/0244467 A1 | 11/2005 | Nivaggioli et al. | |
| 2005/0244470 A1 | 11/2005 | Hughes et al. | |
| 2005/0244475 A1 | 11/2005 | Edelman et al. | |
| 2005/0244477 A1 | 11/2005 | Hughes et al. | |
| 2005/0249710 A1 | 11/2005 | Wong | |
| 2005/0276841 A1 | 12/2005 | Davis et al. | |
| 2005/0281861 A1 | 12/2005 | Hughes et al. | |
| 2006/0009498 A1 | 1/2006 | Whitcup | |
| 2006/0083772 A1 | 4/2006 | DeWitt et al. | |
| 2006/0210604 A1 | 9/2006 | Dadey et al. | |
| 2006/0246112 A1* | 11/2006 | Snyder | A61F 2/147 424/427 |
| 2006/0257450 A1 | 11/2006 | Mudumba et al. | |
| 2006/0257451 A1 | 11/2006 | Varner et al. | |
| 2006/0264453 A1 | 11/2006 | Mudumba et al. | |
| 2007/0031472 A1 | 2/2007 | Huang et al. | |
| 2007/0059336 A1 | 3/2007 | Hughes et al. | |
| 2007/0088014 A1 | 4/2007 | Edelman et al. | |
| 2007/0191863 A1 | 8/2007 | De Juan, Jr. et al. | |
| 2007/0212395 A1 | 9/2007 | Donello et al. | |
| 2007/0233037 A1 | 10/2007 | Gifford, III et al. | |
| 2007/0298073 A1 | 12/2007 | Whitcup et al. | |
| 2007/0298074 A1 | 12/2007 | Robinson et al. | |
| 2008/0038316 A1 | 2/2008 | Wong et al. | |
| 2008/0057101 A1 | 3/2008 | Roorda | |
| 2008/0057102 A1 | 3/2008 | Roorda | |
| 2008/0057103 A1 | 3/2008 | Roorda | |
| 2008/0107694 A1 | 5/2008 | Trogden et al. | |
| 2008/0112923 A1 | 5/2008 | Hughes et al. | |
| 2008/0131484 A1 | 6/2008 | Robinson et al. | |
| 2008/0161741 A1 | 7/2008 | Bene et al. | |
| 2008/0208557 A1 | 8/2008 | Katano | |
| 2008/0228127 A1* | 9/2008 | Burns | A61F 9/00781 604/9 |
| 2008/0292679 A1 | 11/2008 | Lyons et al. | |
| 2009/0036768 A1* | 2/2009 | Seehusen | A61L 29/106 600/424 |
| 2009/0074786 A1 | 3/2009 | Dor et al. | |
| 2009/0082321 A1 | 3/2009 | Edelman et al. | |
| 2009/0118702 A1 | 5/2009 | Lazar | |
| 2009/0123515 A1 | 5/2009 | Taylor et al. | |
| 2009/0148498 A1 | 6/2009 | Libin et al. | |
| 2009/0149947 A1 | 6/2009 | Frohwitter | |
| 2009/0155338 A1 | 6/2009 | Conway et al. | |
| 2009/0157087 A1 | 6/2009 | Wei et al. | |
| 2009/0196906 A1 | 8/2009 | Spada et al. | |
| 2009/0214619 A1 | 8/2009 | Reiff et al. | |
| 2009/0220572 A1 | 9/2009 | Deschatelets et al. | |
| 2009/0280158 A1 | 11/2009 | Butuner | |
| 2009/0286773 A1 | 11/2009 | Spada et al. | |
| 2010/0015195 A1 | 1/2010 | Jain et al. | |
| 2010/0158980 A1 | 6/2010 | Kopczynski et al. | |
| 2010/0204325 A1* | 8/2010 | Blanda et al. | 514/557 |
| 2010/0278898 A1 | 11/2010 | Hughes et al. | |
| 2011/0098640 A1 | 4/2011 | Horne et al. | |
| 2012/0078362 A1 | 3/2012 | Haffner et al. | |
| 2012/0238994 A1 | 9/2012 | Nazzaro et al. | |
| 2013/0062809 A1 | 3/2013 | Ellis et al. | |
| 2013/0289467 A1 | 10/2013 | Haffner et al. | |

FOREIGN PATENT DOCUMENTS

| | | |
|---|---|---|
| WO | WO 2004/073552 A2 | 9/2004 |
| WO | WO 2008/157614 A2 | 12/2008 |
| WO | WO 2009/006370 | 1/2009 |
| WO | WO 2009/063222 A2 | 5/2009 |
| WO | WO 2010/006053 A1 | 1/2010 |
| WO | WO 2010/078063 A1 | 7/2010 |
| WO | WO 2010/135369 | 11/2010 |
| WO | WO 2011/127064 A2 | 10/2011 |

(56) References Cited

FOREIGN PATENT DOCUMENTS

| WO | WO 2012/071476 A2 | 5/2012 |
|---|---|---|
| WO | WO 2014/150292 | 9/2014 |
| WO | WO 2015/073571 | 5/2015 |

OTHER PUBLICATIONS

International Search Report and Written Opinion in PCT/US2014/065283 mailed Feb. 18, 2015.

* cited by examiner

UVEOSCLERAL DRUG DELIVERY IMPLANT AND METHODS FOR IMPLANTING THE SAME

CROSS-REFERENCE TO RELATED APPLICATIONS

This application is the U.S. National Phase application under 35 U.S.C. §371 of International Application No. PCT/US2010/024128, filed on Feb. 12, 2010, which claims the benefit of U.S. Provisional Application No. 61/152,651, filed on Feb. 13, 2009, each of which is incorporated in its entirety by reference herein.

BACKGROUND OF THE INVENTION

Field of the Invention

This disclosure relates to the delivery of a therapeutic agent to ocular tissue via an implant. The disclosure also relates to reducing intraocular pressure within the eye and to a treatment of glaucoma and/or other ocular disorders wherein aqueous humor is permitted to flow out of an anterior chamber of the eye through a surgically implanted pathway.

Description of the Related Art

A human eye is a specialized sensory organ capable of light reception and is able to receive visual images. Aqueous humor is a transparent liquid that fills at least the region between the cornea, at the front of the eye, and the lens. A trabecular meshwork, located in an anterior chamber angle, which is formed between the iris and the cornea, normally serves as a drainage channel for aqueous humor from the anterior chamber so as to maintain a balanced pressure within the anterior chamber of the eye by allowing aqueous humor to flow from the anterior chamber.

About two percent of people in the United States have glaucoma. Glaucoma is a group of eye diseases encompassing a broad spectrum of clinical presentations, etiologies, and treatment modalities. Glaucoma causes pathological changes in the optic nerve, visible on the optic disk, and it causes corresponding visual field loss, resulting in blindness if untreated. Lowering intraocular pressure is the major treatment goal in all glaucomas.

In glaucomas associated with an elevation in eye pressure (intraocular hypertension), the source of resistance to outflow is mainly in the trabecular meshwork. The tissue of the trabecular meshwork normally allows the aqueous humor (hereinafter referred to as "aqueous") to enter Schlemm's canal, which then empties into aqueous collector channels in the posterior wall of Schlemm's canal and then into aqueous veins, which form the episcleral venous system. Aqueous is continuously secreted by a ciliary body around the lens, so there is a constant flow of aqueous from the ciliary body to the anterior chamber of the eye. Pressure within the eye is determined by a balance between the production of aqueous and its exit through the trabecular meshwork (major route) and uveoscleral outflow (minor route). The trabecular meshwork is located between the outer rim of the iris and the back of the cornea, in the anterior chamber angle. The portion of the trabecular meshwork adjacent to Schlemm's canal (the juxtacanilicular meshwork) causes most of the resistance to aqueous outflow.

While a majority of the aqueous leaves the eye through the trabecular meshwork and Schlemm's canal, it is believed that about 10 to about 20 percent of the aqueous in humans leaves through the uveoscleral pathway. The degree with which uveoscleral outflow contributes to the total outflow of the eye appears to be species dependent. As used herein, the term "uveoscleral outflow pathway" is to be given its ordinary and customary meaning to a person of ordinary skill in the art (and it is not to be limited to a special or customized meaning), and refers without limitation to the space or passageway whereby aqueous exits the eye by passing through the ciliary muscle bundles located angle of the anterior chamber and into the tissue planes between the choroid and the sclera, which extend posteriorly to the optic nerve. From these tissue planes, it is believed that the aqueous travels through the surrounding scleral tissue and drains via the scleral and conjunctival vessels, or is absorbed by the uveal blood vessels. It is unclear from studies whether the degree of physiologic uveoscleral outflow is pressure-dependent or pressure-independent. As used herein, the term "supraciliary space" is to be given its ordinary and customary meaning to a person of ordinary skill in the art (and it is not to be limited to a special or customized meaning), and refers without limitation to the portion of the uveoscleral pathway through the ciliary muscle and between the ciliary body and the sclera, and the term "suprachoroidal space" is to be given its ordinary and customary meaning to a person of ordinary skill in the art (and it is not to be limited to a special or customized meaning), and refers without limitation to the portion of the uveoscleral pathway between the choroid and sclera. Although it is not completely understood, some studies have suggested that there may be a "compact zone" of connective tissue associated with the junction between the retina and ciliary body, known as the ora serrata. This "compact zone" may act as a site of resistance along the uveoscleral outflow pathway. The ora serrata can vary in length from about 5.75 mm to 7.5 mm nasally to about 6.5 mm to about 8.5 mm temporally. Other studies suggest that the ciliary muscle bundles are the primary site of resistance.

Certain therapeutic agents have been shown to reduce intraocular pressure by increasing uveoscleral outflow, but the mechanism by which uveoscleral outflow is increased is unclear. Some studies have suggested that relaxation of the ciliary muscle may reduce resistance through the ciliary muscle bundles to increase flow. Other studies suggest that dilation of the post-capillary venules or constriction of the pre-capillary arterioles may reduce downstream fluid pressure and increase uveoscleral outflow.

Glaucoma is broadly classified into two categories: closed-angle glaucoma, also known as angle closure glaucoma, and open-angle glaucoma. Closed-angle glaucoma is caused by closure of the anterior chamber angle by contact between the iris and the inner surface of the trabecular meshwork. Closure of this anatomical angle prevents normal drainage of aqueous from the anterior chamber of the eye. Open-angle glaucoma is any glaucoma in which the exit of aqueous through the trabecular meshwork is diminished while the angle of the anterior chamber remains open. For most cases of open-angle glaucoma, the exact cause of diminished filtration is unknown. Primary open-angle glaucoma is the most common of the glaucomas, and is often asymptomatic in the early to moderately advanced stages of glaucoma. Patients may suffer substantial, irreversible vision loss prior to diagnosis and treatment. However, there are secondary open-angle glaucomas that may include edema or swelling of the trabecular spaces (e.g., from corticosteroid use), abnormal pigment dispersion, or diseases such as hyperthyroidism that produce vascular congestion.

Current therapies for glaucoma are directed toward decreasing intraocular pressure. Currently recognized categories of drug therapy for glaucoma include but are not limited to: (1) Miotics (e.g., pilocarpine, carbachol, and acetylcholinesterase inhibitors), (2) Sympathomimetics (e.g., epinephrine and dipivalylepinephxine), (3) Beta-blockers (e.g., betaxolol, levobunolol and timolol), (4) Carbonic anhydrase inhibitors (e.g., acetazolamide, methazolamide and ethoxzolamide), and (5) Prostaglandins (e.g., metabolite derivatives of arachidonic acid). Medical therapy includes topical ophthalmic drops or oral medications that reduce the production of aqueous or increase the outflow of aqueous. However, drug therapies for glaucoma are sometimes associated with significant side effects. The most frequent and perhaps most serious drawback to drug therapy, especially the elderly, is patient compliance. Patients often forget to take their medication at the appropriate times or else administer eye drops improperly, resulting in under- or overdosing. Patient compliance is particularly problematic with therapeutic agents requiring dosing frequencies of three times a day or more, such as pilocarpine. Because the effects of glaucoma are irreversible, when patients dose improperly, allowing ocular concentrations to drop below appropriate therapeutic levels, further permanent damage to vision occurs. Furthermore, current drug therapies are targeted to be deposited directly into the ciliary body where the aqueous is produced. And current therapies do not provide for a continuous slow-release of the drug. When drug therapy fails, surgical therapy is pursued.

Surgical therapy for open-angle glaucoma consists of laser trabeculoplasty, trabeculectomy, and implantation of aqueous shunts after failure of trabeculectomy or if trabeculectomy is unlikely to succeed. Trabeculectomy is a major surgery that is widely used and is augmented with topically applied anticancer drugs, such as 5-fluorouracil or mitomycin-C to decrease scarring and increase the likelihood of surgical success.

Approximately 100,000 trabeculectomies are performed on Medicare-age patients per year in the United States. This number would likely increase if ocular morbidity associated with trabeculectomy could be decreased. The current morbidity associated with trabeculectomy consists of failure (10-15%); infection (a life long risk of 2-5%); choroidal hemorrhage, a severe internal hemorrhage from low intraocular pressure, resulting in visual loss (1%); cataract formation; and hypotony maculopathy (potentially reversible visual loss from low intraocular pressure). For these reasons, surgeons have tried for decades to develop a workable surgery for redwing intraocular pressure.

The surgical techniques that have been tried and practiced are goniotomy/trabeculotomy and other mechanical disruptions of the trabecular meshwork, such as trabeculopuncture, goniophotoablation, laser trabecular ablation, and goniocurretage. These are all major operations and are briefly described below.

Goniotomy and trabeculotomy are simple and directed techniques of microsurgical dissection with mechanical disruption of the trabecular meshwork. These initially had early favorable responses in the treatment of open-angle glaucoma. However, long-term review of surgical results showed only limited success in adults. In retrospect, these procedures probably failed due to cellular repair and fibrosis mechanisms and a process of "filling in." Filling in is a detrimental effect of collapsing and closing in of the created opening in the trabecular meshwork. Once the created openings close, the pressure builds back up and the surgery fails.

Q-switched Neodynium (Nd) YAG lasers also have been investigated as an optically invasive trabeculopuncture technique for creating full-thickness holes in trabecular meshwork. However, the relatively small hole created by this trabeculopuncture technique exhibits a filling-in effect and fails.

Goniophotoablation is disclosed by Berlin in U.S. Pat. No. 4,846,172 and involves the use of an excimer laser to treat glaucoma by ablating the trabecular meshwork. This method did not succeed in a clinical trial. Hill et al. used an Erbium YAG laser to create full-thickness holes through trabecular meshwork (Hill et al., Lasers in Surgery and Medicine 11:341346, 1991). This laser trabecular ablation technique was investigated in a primate model and a limited human clinical trial at the University of California, Irvine. Although ocular morbidity was zero in both trials, success rates did not warrant further human trials. Failure was again from filling in of surgically created defects in the trabecular meshwork by repair mechanisms. Neither of these is a viable surgical technique for the treatment of glaucoma.

Goniocurretage is an "ab interno" (from the inside), mechanically disruptive technique that uses an instrument similar to a cyclodialysis spatula with a microcurrette at the tip. Initial results were similar to trabeculotomy: it failed due to repair mechanisms and a process of filling in.

Although trabeculectomy is the most commonly performed filtering surgery, viscocanalostomy (VC) and non-penetrating trabeculectomy (NPT) are two new variations of filtering surgery. These are "ab externo" (from the outside), major ocular procedures in which Schlemm's canal is surgically exposed by making a large and very deep scleral flap. In the VC procedure, Schlemm's canal is cannulated and viscoelastic substance injected (which dilates Schlemm's canal and the aqueous collector channels). In the NPT procedure, the inner wall of Schlemm's canal is stripped off after surgically exposing the canal.

Trabeculectomy, VC, and NPT involve the formation of an opening or hole under the conjunctiva and scleral flap into the anterior chamber, such that aqueous is drained onto the surface of the eye or into the tissues located within the lateral wall of the eye. These surgical operations are major procedures with significant ocular morbidity. When trabeculectomy, VC, and NPT are thought to have a low chance for success, a number of implantable drainage devices have been used to ensure that the desired filtration and outflow of aqueous through the surgical opening will continue. The risk of placing a glaucoma drainage device also includes hemorrhage, infection, and diplopia (double vision).

All of the above embodiments and variations thereof have numerous disadvantages and moderate success rates. They involve substantial trauma to the eye and require great surgical skill in creating a hole through the full thickness of the sclera into the subconjunctival space. The procedures are generally performed in an operating room and involve a prolonged recovery time for vision. The complications of existing filtration surgery have prompted ophthalmic surgeons to find other approaches to lowering intraocular pressure or treating tissue of trabecular meshwork.

Because the trabecular meshwork and juxtacanilicular tissue together provide the majority of resistance to the outflow of aqueous, they are logical targets for surgical removal in the treatment of open-angle glaucoma. In addition, minimal amounts of tissue need be altered and existing physiologic outflow pathways can be utilized. Some procedures bypass the trabecular meshwork and juxtacanilicular tissue to drain fluid to physiologic outflow channels. However, in severe cases, it has been found that these procedures do not sufficiently reduce intraocular pressure.

As reported in Arch. Ophthalm. (2000) 118:412, glaucoma remains a leading cause of blindness, and filtration surgery remains an effective, important option in controlling glaucoma. However, modifying existing filtering surgery techniques in any profound way to increase their effectiveness appears to have reached a dead end.

Examples of implantable shunts and surgical methods for maintaining an opening for the release of aqueous from the anterior chamber of the eye to the sclera or space beneath the conjunctiva have been disclosed in, for example, Hsia et al., U.S. Pat. No. 6,059,772 and Baerveldt, U.S. Pat. No. 6,050,970.

Examples of implantable shunts or devices for maintaining an opening for the release of aqueous humor from the anterior chamber of the eye to the sclera or space underneath conjunctiva have been disclosed in U.S. Pat. No. 6,007,511 (Prywes), U.S. Pat. No. 6,007,510 (Nigam), U.S. Pat. No. 5,893,837 (Eagles et al.), U.S. Pat. No. 5,882,327 (Jacob), U.S. Pat. No. 5,879,319 (Pynson et al.), U.S. Pat. No. 5,807,302 (Wandel), U.S. Pat. No. 5,752,928 (de Roulhac et al.), U.S. Pat. No. 5,743,868 (Brown et al.), U.S. Pat. No. 5,704,907 (Nordquist et al.), U.S. Pat. No. 5,626,559 (Solomon), U.S. Pat. No. 5,626,558 (Suson), U.S. Pat. No. 5,601,094 (Reiss), RE. 35,390 (Smith), U.S. Pat. No. 5,558,630 (Fisher), U.S. Pat. No. 5,558,629 (Baerveldt et al.), U.S. Pat. No. 5,520,631 (Nordquist et al.), U.S. Pat. No. 5,476,445 (Baerveldt et al.), U.S. Pat. No. 5,454,796 (Krupin), U.S. Pat. No. 5,433,701 (Rubinstein), U.S. Pat. No. 5,397,300 (Baerveldt et al.), U.S. Pat. No. 5,372,577 (Ungerleider), U.S. Pat. No. 5,370,607 (Memmen), U.S. Pat. No. 5,338,291 (Speckman et al.), U.S. Pat. No. 5,300,020 (L'Esperance, Jr.), U.S. Pat. No. 5,178,604 (Baerveldt et al.), U.S. Pat. No. 5,171,213 (Price, Jr.), U.S. Pat. No. 5,041,081 (Odrich), U.S. Pat. No. 4,968,296 (Ritch et al.), U.S. Pat. No. 4,936,825 (Ungerleider), U.S. Pat. No. 4,886,488 (White), U.S. Pat. No. 4,750,901 (Molteno), U.S. Pat. No. 4,634,418 (Binder), U.S. Pat. No. 4,604,087 (Joseph), U.S. Pat. No. 4,554,918 (White), U.S. Pat. No. 4,521,210 (Wong), U.S. Pat. No. 4,428,746 (Mendez), U.S. Pat. No. 4,402,681 (Haas et al.), U.S. Pat. No. 4,175,563 (Arenberg et al.), and U.S. Pat. No. 4,037,604 (Newkirk).

All of the above embodiments and variations thereof have numerous disadvantages and moderate success rates. They involve substantial trauma to the eye and require great surgical skill in creating a hole through the full thickness of the sclera into the subconjunctival space. The procedures are generally performed in an operating room and involve a prolonged recovery time for vision. The complications of existing filtration surgery have prompted ophthalmic surgeons to find other approaches to lowering intraocular pressure.

SUMMARY OF THE INVENTION

Disclosed herein are systems for treating an ocular disorder in a patient. In one embodiment, the system comprises a drug delivery implant comprising one or more drug delivery portion which, following implantation at an implantation site in the eye, delivers one or more therapeutic agent to one or more of the anterior chamber and the uveoscleral outflow pathway of an eye, and a delivery instrument releasably coupleable to the drug delivery implant for implanting the drug delivery implant. In a preferred embodiment, the instrument is configured to deliver the implant through an insertion site in the sclera to a location in the suprachoroidal space proximate the anterior chamber, and comprises a plurality of members longitudinally moveable relative to each other.

In another embodiment, there is provided a system for treating glaucoma that comprises a plurality of implants configured for implantation into eye tissue, one or more of the implants comprising one or more drug delivery portion which, following implantation at an implantation site in the eye, delivers one or more therapeutic agent to one or more of the anterior chamber and the suprachoroidal space of the eye, and an instrument having a chamber in which the implants are loaded for serial delivery into eye tissue, wherein at least a first implant of the plurality of implants is configured to extend generally alongside a second implant of said plurality of implants.

In another embodiment, there is provided an intraocular implant that comprises a generally elongated body configured for implantation in eye tissue, one or more recess formed in the body and extending from an end of the body generally along an axis, and a therapeutic agent disposed in the recess in a sufficient quantity to treat the eye over a desired period of time and configured to be released to the eye at a desired rate over said period of time. The implant may comprise a lumen extending along the length of the implant about a second axis generally parallel to the axis, the lumen configured to allow flow therethrough.

In another embodiment, there is provided an implant for treating glaucoma that comprises a body configured for implantation in an eye between an anterior chamber and suprachoroidal space of the eye, the body including a therapeutic agent, said body having a lumen extending between an inlet portion and an outlet portion of the body, said inlet portion configured to transport aqueous fluid from the anterior chamber of the eye to the outlet portion, where the outlet portion is disposed in the suprachoroidal space of the eye, said outlet portion having an outflow opening.

Certain embodiments may additionally include one or more of the following features or characteristics: (i) the implant is configured to deliver one or more therapeutic agents to the suprachoroidal space of the uveoscleral outflow pathway; (ii) the instrument and/or device has a sufficiently small cross section such that the insertion site self seals without suturing upon withdrawal of the instrument from the eye; (iii) the implant comprises a lumen extending configured to allow fluid communication between the anterior chamber of the eye and the uveoscleral outflow pathway following implantation of the implant; (iv) at least one of the one or more drug delivery portion comprises at least one of the one or more therapeutic agent compounded with a biodegradable PLGA copolymer, wherein the lactic acid to glycolic acid ratio and/or average molecular weight of the PLGA copolymer is selected to achieve a desired delivery rate of the therapeutic agent over time; (v) a therapeutic agent in fluid communication with the lumen such that the aqueous fluid contacts the therapeutic agent as it flows through the lumen; (vi) a therapeutic agent disposed on an outer surface of the elongated body, where the therapeutic agent is configured to contact ocular tissue following implantation of the drug delivery implant; and (vii) a therapeutic agent compounded with a biodegradable polymer adapted to provide a desired rate of release.

In another embodiment there is provided a method for reducing intraocular pressure in an eye of a mammal, comprising introducing an ocular implant through an incision in ocular tissue, the ocular implant comprising a therapeutic agent and having proximal and distal ends; and advancing the implant to an implantation site in a uveoscleral outflow pathway of the eye such that one of the ends of the implant is in communication with the anterior chamber of the eye and the other of the ends of the implant is in communication with the suprachoroidal space of the eye. Further embodiments may include (i) introducing the implant comprises introducing the implant through an incision in the sclera of the eye made posteriorly of the limbus of the eye, the ocular implant advanced anteriorly into said position in the uveoscleral path, and/or (ii) introducing the implant comprises introducing the implant across the anterior chamber of the eye through an incision at or near a limbus of the eye opposite from the implantation site, advancing the implant across the anterior chamber and posteriorly along the uveoscleral outflow pathway into said implantation site such that the distal end of the implant is located in the suprachoroidal space and the proximal end of the implant is located in the anterior chamber.

BRIEF DESCRIPTION OF THE DRAWINGS

These and other features, aspects, and advantages of the present disclosure will now be described with reference to the drawings of embodiments, which embodiments are intended to illustrate and not to limit the disclosure.

DETAILED DESCRIPTION OF THE PREFERRED EMBODIMENTS

An ophthalmic implant system is provided that comprises a drug delivery implant, which can include a shunt, and a delivery instrument for implanting the drug delivery implant. While this and other systems and associated methods are described herein in connection with glaucoma treatment, the disclosed systems and methods can be used to treat other types of ocular disorders in addition to glaucoma.

Figure 1:
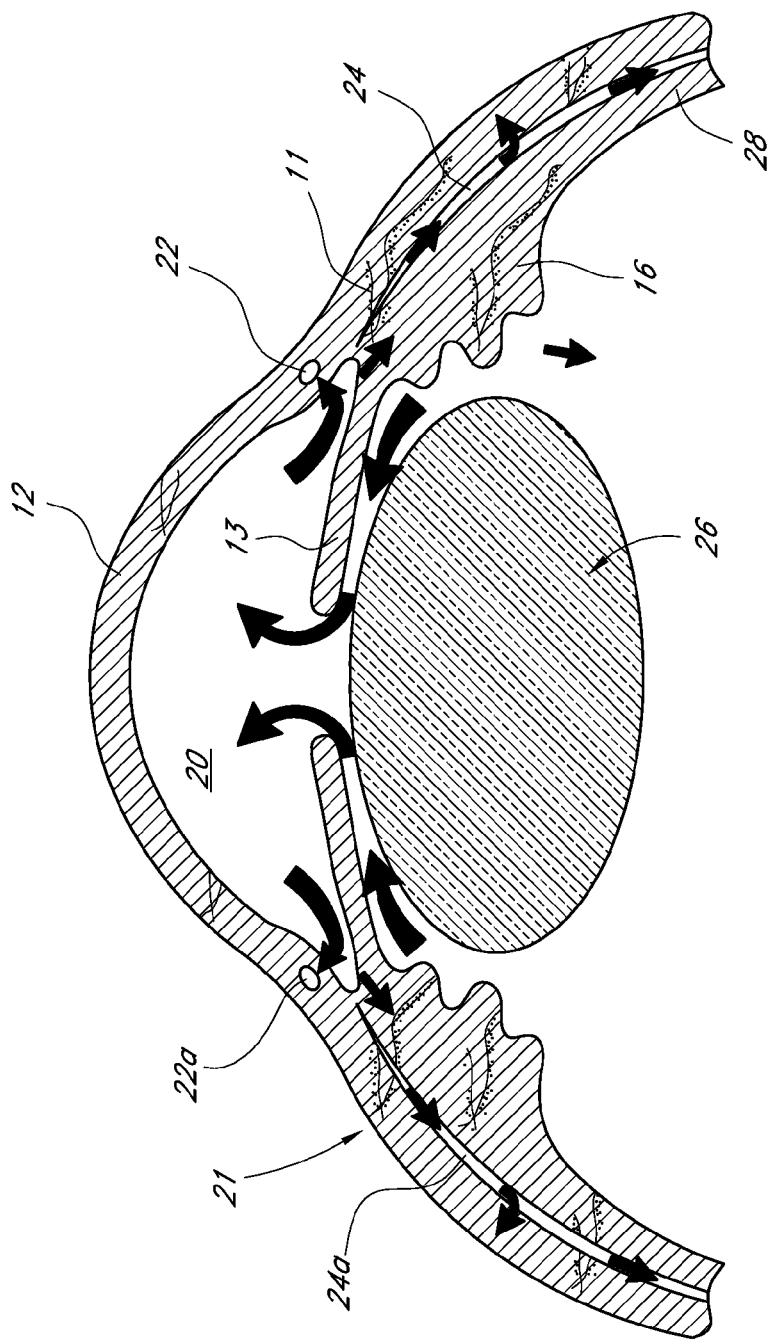
FIG. 1 illustrates a schematic cross-sectional view of an eye.

FIG. 1 illustrates the anatomy of an eye, which includes the sclera 11, which joins the cornea 12 at the limbus 21, the iris 13 and the anterior chamber 20 between the iris 13 and the cornea 12. The eye also includes the lens 26 disposed behind the iris 13, the ciliary body 16 and Schlemm's canal 22. The eye also includes the uveoscleral outflow pathway 24a, which defines the suprachoroidal space 24 between the choroids 28 and the sclera 11.

In embodiments that include the shunt, the shunt, following implantation at an implantation site, can drain fluid from the anterior chamber into a physiologic outflow space. In some embodiments, the shunt can be configured to provide a fluid flow path for draining aqueous humor from the anterior chamber of an eye to the uveoscleral outflow pathway to reduce intraocular pressure. In some embodiments, an instrument is provided for delivering and/or implanting the drainage shunt ab interno in an eye to divert aqueous humor from the anterior chamber to the uveoscleral outflow pathway. In some embodiments, a method is provided for implanting a drainage shunt ab interno in an eye to divert aqueous humor from the anterior chamber to the uveoscleral outflow pathway. In some embodiments, the aqueous humor is diverted to the supraciliary space or the suprachoroidal space of the uveoscleral outflow pathway.

The term "shunt" as used herein is a broad term, and is to be given its ordinary and customary meaning to a person of ordinary skill in the art (and it is not to be limited to a special or customized meaning), and refers without limitation to an implant defining one or more fluid passages. The fluid passage(s) in some embodiments remains patent and, in other embodiments, the passage(s) is fully or partially occluded under at least some circumstances (e.g., at lower intraocular pressure levels). The shunts may feature a variety of characteristics, described in more detail below, which facilitate the regulation of intraocular pressure. The mechanical aspects and material composition of the shunt can be important for controlling the amount and direction of fluid flow. Therefore, various examples of shunt dimensions, features, tip configurations, material flexibility, coatings, and valve design, in accordance with some embodiments of the present disclosure, are discussed in detail below.

The delivery instruments, described in more detail below, may be used to facilitate delivery and/or implantation of the drug delivery implant to the desired location of the eye. The delivery instrument preferably is used to place the implant into a desired position by application of a continual implantation force, by tapping the implant into place using a distal portion of the delivery instrument, or by a combination of these methods. The design of the delivery instruments may take into account, for example, the angle of implantation and the location of the implant relative to an incision. For example, in some embodiments, the delivery instrument may have a fixed geometry, be shape-set, or actuated. In some embodiments, the delivery instrument may have adjunctive or ancillary functions. In some embodiments, the delivery instrument may additionally be used to, for example, inject dye and/or viscoelastic fluid, to dissect, or be used as a guidewire.

In one embodiment, the implant can be advanced through the ciliary attachment tissue, which lies to the posterior of the scleral spur, during implantation. This tissue typically is fibrous or porous, which is relatively easy to pierce or cut with a surgical device, and lies inward of the scleral spur. The implant can be advanced through this tissue and abut against the sclera once the implant extends into the uveoscleral outflow pathway. The implant can then slide within the uveoscleral outflow pathway along the interior wall of the sclera. As the implant is advanced into the uveoscleral outflow pathway and against the sclera, the implant will likely be oriented at an angle with respect to the interior wall of the sclera. The implant is advanced until it reaches the desired implantation site within the uveoscleral outflow pathway. In some embodiments, an implant that includes a shunt is advanced into the ciliary body or ciliary muscle bundles to achieve drainage into the supraciliary space. In other embodiments, the implant with the shunt is advanced through the ciliary body or ciliary muscle bundles to achieve fluid communication between the anterior chamber and the suprachoroidal space. In still other embodiments, the implant with the shunt is advanced into the compact zone or through the compact to drain aqueous humor into the more distal portions of the suprachoroidal space.

Shunts

At least some of the disclosed embodiments include shunts that provide a fluid flow path for conducting aqueous humor from the anterior chamber of an eye to the uveoscleral outflow pathway to reduce intraocular pressure, preferably below episcleral venous pressure without hypotony. The shunts can have an inflow portion and an outflow portion. The outflow portion of the shunt preferably is disposed at or near a distal end of the shunt. When the shunt is implanted, the inflow portion may be sized and configured to reside in the anterior chamber of the eye and the outflow portion may be sized and configured to reside in the uveoscleral outflow pathway. In some embodiments, the outflow portion may be sized and configured to reside in the supraciliary region of the uveoscleral outflow pathway or in the suprachoroidal space.

One or more lumens can extend through the shunt to form at least a portion of the flow path. Preferably, there is at least one lumen that operates to conduct the fluid through the shunt. Each lumen preferably extends from an inflow end to an outflow end along a lumen axis. In some embodiments the lumen extends substantially through the longitudinal center of the shunt. In other embodiments, the lumen can be offset from the longitudinal center of the shunt. In still other embodiments, the flow path can be defined by grooves, channel or reliefs formed on an outer surface of the shunt body.

One or more openings can extend through the wall of the shunt. In some embodiments, the openings can extend through a middle portion of the shunt. In other embodiments the openings can extend through other portions of the shunt. The openings can be one or more of a variety of functions. One such function is that when the shunt is inserted into the suprachoroidal or supraciliary space, the openings provide a plurality of routes through which the aqueous humor can drain. For example, once the shunt is inserted into the eye, if the shunt only has one outflow channel (e.g., one end of a lumen), that outflow channel can be plugged, for example, by the shunt's abutment against the interior surface of the sclera or the outer surface of the choroid. Additionally, the outflow channel can be clogged with tissue that is accumulated or cored during the advancement of the shunt through the fibrous or porous tissue. A plurality of openings can provide a plurality of routes through which the fluid may flow to maintain patency and operability of the drainage shunt. In embodiments where the shunt has a porous body, the openings can define surface discontinuities to assist in anchoring the shunt once implanted.

The shunt in some embodiments can include a distal portion that is sufficiently sharp to pierce eye tissue near the scleral spur of the eye, and that is disposed closer to the outlet portion than to the inlet portion. In some embodiments, the distal portion is located at the distal end of the implant. In another embodiment, the distal portion can be sufficiently blunt so as not to substantially penetrate scleral tissue of the eye. In some embodiments, the shunts have a generally sharpened forward end and are self-trephinating, i.e., self-penetrating, so as to pass through tissue without pre-forming an incision, hole or aperture. The sharpened forward end can be, for example, conical or tapered. The tip can be sufficiently sharp to pierce eye tissue near the scleral spur of the eye. The tip also can be sufficiently blunt so as not to substantially penetrate scleral tissue of the eye. The taper angle of the sharpened end can be, for example, about $30°±15°$ in some embodiments. The radius of the tip can be about 70 to about 200 microns. In other embodiments, where an outlet opening is formed at the distal end of the shunt, the distal portion can gradually increase in cross-sectional size in the proximal direction, preferably at a generally constant taper or radius or in a parabolic manner.

In some embodiments, the body of the shunt can include at least one surface irregularity. The surface irregularity can comprise, for example, a ridge, groove, relief, hole, or annular groove. The surface discontinuities or irregularities can also be formed by barbs or other projections, which extend from the outer surface of the shunt, to inhibit migration of the shunt from its implanted position. In some embodiments, the projections may comprise external ribbing to resist displacement of the shunt. The surface irregularity in some embodiments can interact with the tissue of the interior wall of the sclera and/or with the tissue of the ciliary attachment tissue. In some embodiments, the shunts are anchored by mechanical interlock between tissue and an irregular surface and/or by friction fit. In other embodiments, the shunt includes cylindrical recessed portions (e.g., annular groves) along an elongate body to provide enhanced gripping features during implantation and anchoring following implantation within the eye tissue.

The shunt may also incorporate fixation features, such as flexible radial (i.e., outwardly extending) extensions. The extensions may be separate pieces attached to the shunt, or may be formed by slitting the shunt wall, and thermally forming or mechanically deforming the extensions radially outward. If the extensions are separate pieces, they may be comprised of flexible material such as nitinol or polyimide.

The extensions may be located at the proximal or distal ends of the shunt, or both, to prevent extrusion of the shunt from its intended location. The flexibility of the fixation features will facilitate entry through the corneal incision, and also through the ciliary muscle attachment tissue.

In some embodiments, the body of the shunt has an outlet opening on a side surface to allow fluid flow. In some embodiments, the body of the shunt has a plurality of outlet openings on a side surface to allow fluid flow. In other embodiments, there is a plurality of outlet openings at one end of the shunt, such as the distal end. The openings can facilitate fluid flow through the shunt.

The shunt can in some embodiments have a cap, or tip, at one end. The cap can include a tissue-piercing end and one or more outlet openings. Each of the one or more outlet openings can communicate with at least one of the one or more lumens. In some embodiments the cap can have a conically shaped tip with a plurality of outlet openings disposed proximal of the tip's distal end. In other embodiments, the cap can have a tapered angle tip. The tip can be sufficiently sharp to pierce eye tissue near the scleral spur of the eye. The tip also can be sufficiently blunt so as not to substantially penetrate scleral tissue of the eye. In some embodiments, the conically shaped tip facilitates delivery of the shunt to the desired location. In some embodiments, the cap has an outlet opening on a side surface to allow fluid flow. In some embodiments, the cap has a plurality of outlet openings on a side surface to allow fluid flow. In other embodiments, there is a plurality of outlet openings on the conical surface of the cap. The openings on the cap can facilitate fluid flow through the shunt. The opening may provide an alternate route for fluid flow which is beneficial in case the primary outflow portion of the shunt becomes blocked.

In some embodiments, multiple shunts are configured to be delivered during a single procedure. In some embodiments when multiple shunts are delivered, the shunts can be arranged tandemly. In one embodiment, the shunt can include a tip protector at one end. The tip protector can comprise a recess shaped to receive and protect, for example, the tip of an adjacent shunt. In some embodiments, the tip of the adjacent shunt has a conical shape. The recess may be shaped to contact the sides of the conical tip while protecting the more tapered tip, or end, from impact. The tip protector is particularly useful for delivery of multiple shunts.

The shunts may be of varied lengths to optimize flows. In some preferred embodiments, the shunt has sufficient length such that the outflow portion resides in the suprachoroidal space and the inflow portion is exposed to the anterior chamber. In other preferred embodiments, the length of the shunt is a length such that the outflow portion resides in the supraciliary space of the uveoscleral outflow pathway. In some embodiments, the length of the shunt is a length such that the outflow portion resides in the membranous region of the uveoscleral outflow pathway adjacent to the retina, while in other embodiments, the shunt has a length that extends distally past the membranous region. In some embodiments, the length of the shunt from the portion residing in the anterior chamber to the portion residing in the uveoscleral outflow pathway may be about 0.5 mm to about 5 mm. In preferred embodiments, the length of the shunt may be about 1.5 mm to about 5 mm. In more preferred embodiments, the length of the shunt may be about 2.0 mm. In some embodiments, the length of the shunt is about 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0 mm.

In some embodiments, the shunt can have an outer diameter that will permit the shunt to fit within a 23-gauge needle during implantation. The shunt can also have a diameter that is designed to be inserted with larger needles. For example, the shunt can also be delivered with 18-, 19- or 20-gauge needles. In other embodiments, smaller gauge applicators, such as a 23-gauge (or smaller) applicator, may be used. The shunt can have a substantially constant cross-sectional shape through most of the length of the shunt, or the shunt can have portions of reduced or enlarged cross-sectional size (e.g., diameter), or cylindrical channels, e.g., annular grooves, disposed on the outer surface between the proximal end and the distal end. The distal end of the shunt can have a tapered portion, or a portion having a continually decreasing radial dimension with respect to the lumen axis along the length of the axis. The tapered portion preferably in some embodiments terminates with a smaller radial dimension at the outflow end. During implantation, the tapered portion can operate to form, dilate, and/or increase the size of, an incision or puncture created in the tissue. The tapered portion may have a diameter of about 23 gauge to about 30 gauge, and preferably about 25 gauge. However, other dimensions are possible.

The diameter of one or more drainage lumens within the shunt may be varied to alter flow characteristics. The cross-sectional size of a shunt may be, for example, 0.1 mm to about 1.0 mm, or preferably about 0.3 mm to about 0.4 mm. A small cross-sectional size can be used to restrict flow. The cross-sectional shape of the shunt or a shunt may be any of a variety of cross-sectional shapes suitable for allowing fluid flow. For example, the cross-sectional shape of the shunt or shunt may be circular, oval, square, trapezoidal, rectangular, or any combination thereof.

In some embodiments, the shunt is configured to expand, either radially or axially, or both radially and axially. In some embodiments, the shunt may be self-expanding. In other embodiments, the shunt may be expanded by, for example, using a balloon device.

In some embodiments, the structure of the shunt may be flexible. At least a portion of the structure of the shunt may be flexible, or the whole structure may be flexible. In some embodiments, the structure of the shunt is accordion- or balloon-like. This pleated like structure provides flexibility. In other embodiments, at least a portion of the shunt is curved. In some embodiments, at least a portion of the shunt is straight. In some embodiments, the shunt has both curved and straight portions, and in some embodiments, the shunt is generally rigid (i.e., maintains its preformed shape when implanted).

The shunt is preferably made of one or more biocompatible materials. Suitable biocompatible materials include, for example, polypropylene, polyimide, glass, nitinol, polyvinyl alcohol, polyvinyl pyrolidone, collagen, chemically-treated collagen, polyethersulfone (PES), poly(styrene-isobutyl-styrene), Pebax, acrylic, polyolefin, polysilicon, polypropylene, hydroxyapetite, titanium, gold, silver, platinum, other metals, ceramics, plastics and a mixture thereof. The shunts can be manufactured by conventional sintering, micro machining, laser machining, and/or electrical discharge machining. However, other suitable manufacturing methods can be used In some embodiments, the shunt is made of a flexible material. In other embodiments, the shunt is made of a rigid material. In some embodiments, a portion of the shunt is made from flexible material while another portion of the shunt is made from rigid material. The body can have an outer surface of which at least a portion is porous. Some embodiments include porosity that can be varied by masking a portion of the exterior with a band. Where the shunts include a porous body, the cross-section and porosity can be calibrated (down to 0.5 micrometers) to control the flow rates of aqueous humor through the shunt.

In some embodiments, at least a portion of the shunt (e.g., an internal spine or an anchor) is made of a material capable of shape memory. A material capable of shape memory may be compressed and, upon release, may expand axially or radially, or both axially and radially, to assume a particular shape. In some embodiments, at least a portion of the shunt has a preformed shape. In other embodiments, at least a portion of the shunt is made of a superelastic material. In some embodiments, at least a portion of the shunt is made up nitinol. In other embodiments, at least a portion of the shunt is made of a deformable material.

In some embodiments, the body of the shunt can comprise material that includes a therapeutic agent, and/or can house, anchor, or support a therapeutic agent, or can include a coating. The coating can include a therapeutic agent. The coatings can be, for example, a drug eluting coating, an antithrombogenic coating, and a lubricious coating. The therapeutic agent can be selected from the group consisting of: heparin, TGF-beta, an intraocular pressure-lowering drug, and an anti-proliferative agent. Materials that may be used for a drug-eluting coating include parylene C, poly (butyl methacrylate), poly (methyl methacrylate), polyethylene-co-vinyl acetate, and other materials known in the art.

In some embodiments, the shunt can further comprise a biodegradable material in or on the shunt. Such biodegradable copolymers may be situated within a lumen of the shunt, on the tip of the shunt, or on the cap of the shunt. In some embodiments, at least a portion of the shunt itself may comprise a biodegradable material. Still other embodiments may comprise a shunt made entirely of a biodegradable material, such that the entire shunt is degraded over time. The biodegradable material can be any suitable material including, but not limited to, poly(lactic acid), polyethylene-vinyl acetate, poly(lactic-co-glycolic acid), poly(D,L-lactide), poly(D,L-lactide-co-trimethylene carbonate), collagen, heparinized collagen, poly(caprolactone), poly(glycolic acid), and/or other polymer or copolymer. All or a portion of the shunt may be coated with a therapeutic agent, e.g. with heparin, preferably in the flow path, to reduce blood thrombosis or tissue restenosis. The biodegradable material may also include a therapeutic agent, such as a drug, mixed or compounded therein such that the therapeutic agent is released as the biodegradable material degrades or erodes following implantation.

The biodegradable material used in the shunt or any other device disclosed herein includes any suitable material that degrades or erodes over time when placed in the human or animal body. Accordingly, as the term is used herein, biodegradable material includes bioerodible materials. Biodegradable materials may be advantageously used to deliver one or more drugs or therapeutic agents. Therefore, it will be understood that embodiments incorporating a therapeutic agent as described herein can include having the therapeutic agent compounded with a biodegradable material or other agent modifying the release characteristics of the therapeutic agent.

One or more therapeutic agents may be compounded with one or more types of biodegradable polymers (including copolymers), providing release of the therapeutic agent(s) as the polymer degrades or erodes in vivo. Depending on the ocular disorder to be treated and the placement of the device in the eye, it may be advantageous to place a biodegradable polymer incorporating a therapeutic agent at different locations in or on the device, such that the therapeutic agent(s) may be released at a target site or region of the eye. Devices comprising biodegradable polymer with a therapeutic agent may also be coated (fully or partially) with one or more coatings comprising one or more drugs or other therapeutic agent(s).

Preferred biodegradable materials include copolymers of lactic acid and glycolic acid, also known as poly (lactic-co-glycolic acid) or PLGA. It will be understood by one skilled in the art that although some disclosure herein specifically describes use of PLGA, other suitable biodegradable materials may be substituted for PLGA or used in combination with PLGA in such embodiments. It may be desirable, in some embodiments, to provide for a particular rate of release of therapeutic agent from a PLGA copolymer. As the release rate of a therapeutic agent from a PLGA copolymer correlates with the degradation rate of that copolymer, control of the degradation rate provides a means for control of the delivery rate of a therapeutic agent. Variation of the average molecular weight of the polymer or copolymer chains which make up the PLGA copolymer can be used to control the degradation rate of the copolymer, thereby achieving a desired duration or other release profile of therapeutic agent delivery to the eye. In certain other embodiments employing PLGA copolymers, rate of biodegradation of the PLGA copolymer may be controlled by varying the ratio of lactic acid to glycolic acid units in a copolymer. Still other embodiments may utilize combinations of varying the average molecular weights of the constituents of the copolymer and varying the ratio of lactic acid to glycolic acid in the copolymer to achieve a desired biodegradation rate. In addition, as described in more detail below, the incorporation of a copolymer in or on a device in a particular location may affect the biodegradation rate of the copolymer, thus providing another means of controlling the release rate of the therapeutic agent.

In some ocular disorders, therapy may require a defined kinetic profile of administration of therapeutic agents to the eye. In certain embodiments, devices made from PLGA copolymers or which incorporate PLGA copolymers, wherein the copolymer is compounded with a therapeutic agent, may provide particular kinetic profiles of release of such therapeutic agent. By tailoring the ratio of lactic to glycolic acid in a copolymer and/or average molecular weight of polymers or copolymers having the therapeutic agent therein, sustained release of a therapeutic agent, or other desirable release profile, may be achieved. In certain embodiments, zero-order release of a therapeutic agent may be achieved by tailoring the ratio of lactic to glycolic acid and/or average molecular weights in the copolymer composition so that that the biodegradation of the PLGA copolymer is the principal factor controlling therapeutic agent release from the copolymer. In certain embodiments, pseudo zero-order release (or other desired release profile) may be achieved by using multiple PLGA copolymer formulations in or on one or more devices, each copolymer formulation achieving a different therapeutic agent release profile such that the additive effect over time replicates true zero-order kinetics. For example, a series of devices or a single device having multiple regions incorporating PLGA with one or more therapeutic agents may be delivered to the eye, wherein the devices or regions incorporate at least two different PLGA copolymer formulations. As each copolymer biodegrades or erodes at its individual and desired rate, the sum total of therapeutic agent released to the eye over time is in effect released with zero-order kinetics.

Non-continuous or pulsatile release may also be desirable. This may be achieved, for example, by incorporating multiple PLGA formulations with varying biodegradation rates into a single device or a series of devices so that, with clearance of a therapeutic agent from the eye and/or varying rates of release of therapeutic agent from the copolymers results in a concentration of a therapeutic agent that is not constant over time.

The flow path through the shunt can be configured to be regulated to a flow rate that will reduce the likelihood of hypotony in the eye. In some embodiments, the intraocular pressure is maintained at about 8 mm Hg. In other embodiments, the intraocular pressure is maintained at pressures less than about 8 mmHg, for example the intraocular pressure may be maintained between about 6 mm Hg and about 8 mm Hg. In other embodiments, the intraocular pressure is maintained at pressures greater than about 8 mm Hg. For example, the pressures may be maintained between about 8 mmHg and about 18 mm Hg, and more preferably between 8 mm Hg and 16 mm Hg, and most preferably not greater than 12 mm Hg. In some embodiments, the flow rate can be limited to about 2.5 µL/min or less. In some embodiments the flow rate can be limited to between about 1.9 µL/min and about 3.1 µL/min.

For example, the Hagen-Poiseuille equation suggests that a 4 mm long stent at a flow rate of 2.5 µL/min should have an inner diameter of 52 µm to create a pressure gradient of 5 mm Hg above the pressure in the suprachoroidal space.

The shunt may or may not include a mechanism for regulating fluid flow through the shunt. Mechanisms for regulating fluid flow can include flow restrictors, pressure regulators, or both. Alternatively, in some embodiments the shunt has neither a flow restrictor nor a pressure regulator. Regulating flow of aqueous humor can comprise varying between at least first and second operational states in which aqueous humor flow is more restricted in a first state and less restricted in a second state. Increasing the restriction to flow when changing from the second state to the first state can involve moving a valve toward a valve seat in a direction generally parallel or generally normal to a line connecting the proximal and distal ends of the shunt.

As noted above, the outflow portion of the shunt, in some embodiments is sized and configured to reside in the supraciliary region of the uveoscleral outflow pathway. In such embodiments, there is a lesser need for a mechanism for regulating fluid flow through the shunt.

The mechanism for flow restriction may be, for example, a valve, a long lumen length, small lumen cross section, or any combination thereof. In some embodiments, the flow of fluid is restricted by the size of a lumen within the shunt, which produces a capillary effect that limits the fluid flow for given pressures. The capillary effect of the lumen allows the shunt to restrict flow and provides a valveless regulation of fluid flow.

In one embodiment, the flow path length may be increased without increasing the overall length of the shunt by creating a lumen with a spiral flow path. A lumen within the shunt is configured to accommodate placement therein of a spiral flow channel core that is configured to provide preferred flow restriction. In effect, the spiral flow channel provides an extended path for the flow of fluid between the inlet(s) and outlet(s) of the shunt that is greater than a straight lumen extending between the ends of the shunt. The extended path provides a greater potential resistance of fluid flow through the shunt without increasing the length of the shunt. The core could have a single spiral flow channel, or a plurality of spiral flow channels for providing a plurality of flow paths through which fluid may flow through the shunt. For example, the core can have two or more spiral flow channels, which can intersect.

In some embodiments, the mechanism for flow regulation can include a pressure regulating valve. In one embodiment, the valve can open when fluid pressure within the anterior chamber exceeds a predetermined level (e.g., a preset pressure). Intraocular pressure may be used to apply a force to move a valve surface within the shunt in a direction transverse to a longitudinal axis of the shunt such that aqueous humor flows from the anterior chamber to the uveoscleral outflow pathway at intraocular pressures greater than a threshold pressure.

In some embodiments, the shunt may have any number of valves to restrict flow and/or regulate pressure. The valve can be located between the anterior chamber and one or more effluent openings such that movement of the valve regulates flow from the anterior chamber to the one or more effluent openings. A variety of valves are useful with the shunt for restricting flow. In some embodiments, the valve is a unidirectional valve and/or is a pressure relief valve. The pressure relief valve can comprise a ball, a ball seat and a biasing member urging the ball towards the ball seat. In some embodiments, the valve is a reed-type valve. In a reed valve, for example, one end of the valve may be fixed to a portion of the shunt. The body of the reed valve can be deflected in order to allow flow through the valve. Pressure from fluid in the anterior chamber can deflect the body of the reed valve, thereby causing the valve to open.

In some embodiments, the shunt can include a pressure regulation valve having a deflectable plate or diaphragm with a surface area exposed to fluid within the anterior chamber, the surface area being substantially greater than the total cross-sectional flow area of the one or more influent openings of the shunt. Such a valve can be disposed between an anterior chamber of the shunt and the one or more effluent openings such that movement of the deflectable plate regulates flow from the anterior chamber to the one or more effluent openings. The plate can extend in a direction generally parallel to the inlet flow path and to the outlet flow path.

When the intraocular pressure exceeds a predetermined pressure, the check pressure relief valve can open and permit fluid to flow between the anterior chamber and the uveoscleral outflow pathway. When the intraocular pressure decreases to a second, lower pressure, the valve can close to limit or inhibit fluid from flowing to the suprachoroidal space. In one embodiment, the valve can remain closed until the intraocular pressure again reaches the predetermined pressure, at which time the valve can reopen to permit or enhance drainage of fluid to the uveoscleral outflow pathway. Accordingly, the shunt can provide drainage of the anterior chamber through the shunt based on the intraocular pressure levels and reduce the likelihood for over-draining the anterior chamber and causing hypotony.

Delivery Instruments

Another aspect of the systems and methods described herein relates to delivery instruments for implanting the drug delivery implant, which may include a shunt for draining fluid from the anterior chamber into a physiologic outflow space. In some embodiments, the drug delivery implant is inserted from a site transocularly situated from the implantation site. The delivery instrument can be sufficiently long to advance the implant transocularly from the insertion site across the anterior chamber to the implantation site. At least a portion of the instrument can be flexible. Alternatively, in other embodiments the instrument can be rigid. The instrument can include a plurality of members longitudinally moveable relative to each other. In some embodiments, at least a portion of the delivery instrument is curved or angled. In some embodiments, a portion of the delivery instrument is rigid and another portion of the instrument is flexible.

In some embodiments, the delivery instrument has curved distal portion. The curvature of the distal portion of the delivery instrument can have as a radius of between about 10 mm and about 30 mm, and preferably about 20 mm.

In some embodiments, the delivery instrument can have an angled distal segment. For example, the angle of the distal segment can be between about 90° and about 170° relative to an axis of the proximal segment of the delivery instrument, and preferably about 145°. In one embodiment, the angle can incorporate a small radius of curvature at the "elbow" between the proximal and distal segments so as to define a smooth transition from the proximal segment of the delivery instrument to the distal segment. In one embodiment, the length of the distal segment may be between approximately 0.5 to 7 mm, and preferably about 2 to 3 mm. However, the distal segment of the delivery instrument can have other suitable lengths.

In some embodiments, the instrument can have a sharpened forward end and be self-trephinating, i.e., self-penetrating, so as to pass through tissue without pre-forming an incision, hole or aperture. Alternatively, a trocar, scalpel, or similar instrument can be used to pre-form an incision in the eye tissue before passing the implant into such tissue.

For delivery of some embodiments of the drug delivery implant, the instrument can have a sufficiently small cross section such that the insertion site self seals without suturing upon withdrawal of the instrument from the eye. In one embodiment, an outer diameter of the delivery instrument is preferably no greater than about 18 gauge and not smaller than about 27 gauge. However, the delivery instrument can have other suitable outer diameter dimensions.

For delivery of some embodiments of the drug delivery implant, the incision in the corneal tissue is preferable made with a hollow needle through which the implant can be passed. The needle can have a small diameter size (e.g., 18 or 19 or 20 or 21 or 22 or 23 or 24 or 25 or 26 or 27 gauge) so that the incision is self sealing and the implantation occurs in a closed chamber with or without viscoelastic. A self-sealing incision also can be formed using a conventional "tunneling" procedure in which a spatula-shaped scalpel is used to create a generally inverted V-shaped incision through the cornea. In a preferred mode, the instrument used to form the incision through the cornea remains in place (that is, extends through the corneal incision) during the procedure and is not removed until after implantation. Such incision-forming instrument either can be used to carry the implant or can cooperate with a delivery instrument to allow implantation through the same incision without withdrawing the incision-forming instrument. Of course, in other embodiments, various surgical instruments can be passed through one or more corneal incisions multiple times.

Once into the anterior chamber, a delivery instrument can be advanced from the insertion site transocularly into the anterior chamber angle and positioned at a location near the scleral spur. Using the scleral spur as a reference point, the delivery instrument can be advanced further in a generally posterior direction to drive the implant into the uveoscleral pathway. The placement and implantation of the implant can be performed using a gonioscope or other conventional imaging equipment. The delivery instrument preferably is used to force the implant into a desired position by application of a continual implantation force, by tapping the implant into place using a distal portion of the delivery instrument, or by a combination of these methods. Once the implant is in the desired position, it may be further seated by tapping using a distal portion of the delivery instrument.

In one embodiment, the delivery instrument can include an open distal end with a lumen extending therethrough. Positioned within the lumen is preferably a pusher tube that is axially movable within the lumen. The pusher tube can be any device suitable for pushing or manipulating the implant in relation to the delivery instrument, such as, for example, but without limitation a screw, a rod, a stored energy device such as a spring. A wall of the delivery instrument can extend beyond pusher tube to accommodate placement within the lumen of a drug delivery implant. The implant can be secured in position. For example, the implant can be secured by viscoelastic or mechanical interlock with the pusher tube or wall. When the implant is brought into position adjacent the uveoscleral pathway in the anterior chamber angle, the pusher tube is advanced axially toward the open distal end of the delivery instrument. As the pusher tube is advanced, the implant is also advanced. When the implant is advanced into the uveoscleral pathway and such that it is no longer in the lumen of the delivery instrument, the delivery instrument can be retracted, leaving the drug delivery implant in the uveoscleral pathway.

Some embodiments can include a spring-loaded or stored-energy pusher system. The spring-loaded pusher preferably includes a button operably connected to a hinged rod device. The rod of the hinged rod device engages a depression in the surface of the pusher, keeping the spring of the pusher in a compressed conformation. When the user pushes the button, the rod is disengaged from the depression, thereby allowing the spring to decompress, thereby advancing the pusher forward.

In some embodiments, an over-the wire system can be used to deliver the drug delivery implant. The implant can be delivered over a wire. Preferably, the wire is self-trephinating. In one embodiment, the wire can function as a trocar. The wire can be superelastic, flexible, or relatively inflexible with respect to the implant. The wire can be pre-formed to have a certain shape. The wire can be curved. The wire can have shape memory, or be elastic. In some embodiments, the wire is a pull wire. The wire can be a steerable catheter.

In some embodiments, the wire is positioned within a lumen in the drug delivery implant, such as a lumen of a shunt of the implant. The wire can be axially movable within the lumen. The lumen may or may not include valves or other flow regulatory devices.

In some embodiments, the delivery instrument is a trocar. The trocar may be angled or curved. The trocar can be rigid, semi-rigid or flexible. In embodiments where the trocar can be stiff, the implant can be, but need not be relatively flexible. The diameter of the trocar can be about 0.001 inches to about 0.01 inches. In some embodiments, the diameter of the trocar is 0.001, 0.002, 0.004, 0.005, 0.006, 0.007, 0.008, 0.009, or 0.01 inches.

In some embodiments, delivery of the drug delivery implant is achieved by applying a driving force at or near the distal end of the implant. The driving force can be a pulling or a pushing applied generally to the end of the implant.

The instrument can include a seal to prevent aqueous humor from passing through the delivery instrument and/or between the members of the instrument when the instrument is in the eye. The seal can also aid in preventing backflow of aqueous humor through the instrument and out the eye.

Suitable seals for inhibiting leakage include, for example, an o-ring, a coating, a hydrophilic agent, a hydrophobic agent, and combinations thereof. The coating can be, for example, a silicone coat such as MDX™ silicone fluid. In some embodiments, the instrument is coated with the coating and a hydrophilic or hydrophobic agent. In some embodiments, one region of the instrument is coated with the coating plus the hydrophilic agent, and another region of the instrument is coated with the coating plus the hydrophobic agent. The delivery instrument can additionally comprise a seal between various members comprising the instrument. The seal can comprise a hydrophobic or hydrophilic coating between slip-fit surfaces of the members of the instrument. The seal can be disposed proximate of the drug delivery implant when carried by the delivery instrument. Preferably, the seal is present on at least a section of each of two devices that are machined to fit closely with one another.

In some embodiments, the delivery instrument can include a distal end having a beveled shape. The delivery instrument can include a distal end having a spatula shape. The beveled or spatula shape can have a sharpened edge. The beveled or spatula shape can include a recess to contain the drug delivery implant. The recess can include a pusher or other suitable means to push out or eject the implant.

The delivery instrument further can be configured to deliver multiple drug delivery implants. In some embodiments, when multiple drug delivery implants are delivered, the implants can be arranged in tandem, as described in greater detail below.

Therapeutic Agents

The therapeutic agents utilized with the drug delivery implant, may include one or more drugs provided below, either alone or in combination. The drugs utilized may also be the equivalent of, derivatives of, or analogs of one or more of the drugs provided below. The drugs may include but are not limited to pharmaceutical agents including anti-glaucoma medications, ocular agents, antimicrobial agents (e.g., antibiotic, antiviral, antiparasitic, antifungal agents), anti-inflammatory agents (including steroids or non-steroidal anti-inflammatory), biological agents including hormones, enzymes or enzyme-related components, antibodies or antibody-related components, oligonucleotides (including DNA, RNA, short-interfering RNA, antisense oligonucletides, and the like), DNA/RNA vectors, viruses (either wild type or genetically modified) or viral vectors, peptides, proteins, enzymes, extracellular matrix components, and live cells configured to produce one or more biological components. The use of any particular drug is not limited to its primary effect or regulatory body-approved treatment indication or manner of use. Drugs also include compounds or other materials that reduce or treat one or more side effects of another drug or therapeutic agent. As many drugs have more than a single mode of action, the listing of any particular drug within any one therapeutic class below is only representative of one possible use of the drug and is not intended to limit the scope of its use with the ophthalmic implant system.

Examples of drugs may include various anti-secretory agents; antimitotics and other anti-proliferative agents, including among others, anti-angiogenesis agents such as angiostatin, anecortave acetate, thrombospondin, VEGF receptor tyrosine kinase inhibitors and anti-vascular endothelial growth factor (anti-VEGF) drugs such as ranibizumab (LUCENTIS®) and bevacizumab (AVASTIN®), pegaptanib (MACUGEN®), sunitinib and sorafenib and any of a variety of known small-molecule and transcription inhibitors having anti-angiogenesis effect; classes of known ophthalmic drugs, including: glaucoma agents, such as adrenergic antagonists, including for example, beta-blocker agents such as atenolol propranolol, metipranolol, betaxolol, carteolol, levobetaxolol, levobunolol and timolol; adrenergic agonists or sympathomimetic agents such as epinephrine, dipivefrin, clonidine, aparclonidine, and brimonidine; parasympathomimetics or cholingeric agonists such as pilocarpine, carbachol, phospholine iodine, and physostigmine, salicylate, acetylcholine chloride, eserine, diisopropyl fluorophosphate, demecarium bromide); muscarinics; carbonic anhydrase inhibitor agents, including topical and/or systemic agents, for example acetozolamide, brinzolamide, dorzolamide and methazolamide, ethoxzolamide, diamox, and dichlorphenamide; mydriatic-cycloplegic agents such as atropine, cyclopentolate, succinylcholine, homatropine, phenylephrine, scopolamine and tropicamide; prostaglandins such as prostaglandin F2 alpha, antiprostaglandins, prostaglandin precursors, or prostaglandin analog agents such as bimatoprost, latanoprost, travoprost and unoprostone.

Other examples of drugs may also include anti-inflammatory agents including for example glucocorticoids and corticosteroids such as betamethasone, cortisone, dexamethasone, dexamethasone 21-phosphate, methylprednisolone, prednisolone 21-phosphate, prednisolone acetate, prednisolone, fluorometholone, loteprednol, medrysone, fluocinolone acetonide, triamcinolone acetonide, triamcinolone, triamcinolone acetonide, beclomethasone, budesonide, flunisolide, fluorometholone, fluticasone, hydrocortisone, hydrocortisone acetate, loteprednol, rimexolone and non-steroidal anti-inflammatory agents including, for example, diclofenac, flurbiprofen, ibuprofen, bromfenac, nepafenac, and ketorolac, salicylate, indomethacin, ibuprofen, naxopren, piroxicam and nabumetone; anti-infective or antimicrobial agents such as antibiotics including, for example, tetracycline, chlortetracycline, bacitracin, neomycin, polymyxin, gramicidin, cephalexin, oxytetracycline, chloramphenicol, rifampicin, ciprofloxacin, tobramycin, gentamycin, erythromycin, penicillin, sulfonamides, sulfadiazine, sulfacetamide, sulfamethizole, sulfisoxazole, nitrofurazone, sodium propionate, aminoglycosides such as gentamicin and tobramycin; fluoroquinolones such as ciprofloxacin, gatifloxacin, levofloxacin, moxifloxacin, norfloxacin, ofloxacin; bacitracin, erythromycin, fusidic acid, neomycin, polymyxin B, gramicidin, trimethoprim and sulfacetamide; antifungals such as amphotericin B and miconazole; antivirals such as idoxuridine trifluorothymidine, acyclovir, gancyclovir, interferon; antimicotics; immune-modulating agents such as anti-allergenics, including, for example, sodium chromoglycate, antazoline, methapyriline, chlorpheniramine, cetrizine, pyrilamine, prophenpyridamine anti-histamine agents such as azelastine, emedastine and levocabastine; immunological drugs (such as vaccines and immune stimulants); MAST cell stabilizer agents such as cromolyn sodium, ketotifen, lodoxamide, nedocrimil, olopatadine and pemirolastciliary body ablative agents, such as gentimicin and cidofovir; and other ophthalmic agents such as verteporfin, proparacaine, tetracaine, cyclosporine and pilocarpine; inhibitors of cell-surface glycoprotein receptors; decongestants such as phenylephrine, naphazoline, tetrahydrazoline; lipids or hypotensive lipids; dopaminergic agonists and/or antagonists such as quinpirole, fenoldopam, and ibopamine; vasospasm inhibitors; vasodilators; antihypertensive agents; angiotensin converting enzyme (ACE) inhibitors; angiotensin-1 receptor antagonists such as olmesartan; microtubule inhibitors; molecular motor (dynein and/or kinesin) inhibitors; actin cytoskeleton regulatory agents such as cyctchalasin, latrunculin, swinholide A, ethacrynic acid, H-7, and Rho-kinase (ROCK) inhibitors; remodeling inhibitors; modulators of the extracellular matrix such as tert-butylhydro-quinolone and AL-3037A; adenosine receptor agonists and/or antagonists such as N-6-cylclophexyladenosine and (R)-phenylisopropyladenosine; serotonin agonists; hormonal agents such as estrogens, estradiol, progestational hormones, progesterone, insulin, calcitonin, parathyroid hormone, peptide and vasopressin hypothalamus releasing factor; growth factor antagonists or growth factors, including, for example, epidermal growth factor, fibroblast growth factor, platelet derived growth factor, transforming growth factor beta, somatotrapin, fibronectin, connective tissue growth factor, bone morphogenic proteins (BMPs); cytokines such as interleukins, CD44, cochlin, and serum amyloids, such as serum amyloid A.

Other therapeutic agents may include neuroprotective agents such as lubezole, nimodipine and related compounds, and including blood flow enhancers, sodium channels blockers, glutamate inhibitors such as memantine, neurotrophic factors, nitric oxide synthase inhibitors; free radical scavengers or anti-oxidants; chelating compounds; apoptosis-related protease inhibitors; compounds that reduce new protein synthesis; radiotherapeutic agents; photodynamic therapy agents; gene therapy agents; genetic modulators; and dry eye medications such as cyclosporine A, delmulcents, and sodium hyaluronate.

Other therapeutic agents that may be used include: other beta-blocker agents such as acebutolol, atenolol, bisoprolol, carvedilol, asmolol, labetalol, nadolol, penbutolol, and pindolol; other corticosteroidal and non-steroidal anti-inflammatory agents such aspirin, betamethasone, cortisone, diflunisal, etodolac, fenoprofen, fludrocortisone, flurbiprofen, hydrocortisone, ibuprofen, indomethacine, ketoprofen, meclofenamate, mefenamic acid, meloxicam, methylprednisolone, nabumetone, naproxen, oxaprozin, prednisolone, prioxicam, salsalate, sulindac and tolmetin; COX-2 inhibitors like celecoxib, rofecoxib and. Valdecoxib; other immune-modulating agents such as aldesleukin, adalimumab (HUMIRA®), azathioprine, basiliximab, daclizumab, etanercept (ENBREL®), hydroxychloroquine, infliximab (REMICADE®), leflunomide, methotrexate, mycophenolate mofetil, and sulfasalazine; other anti-histamine agents such as loratadine, desloratadine, cetirizine, diphenhydramine, chlorpheniramine, dexchlorpheniramine, clemastine, cyproheptadine, fexofenadine, hydroxyzine and promethazine; other anti-infective agents such as aminoglycosides such as amikacin and streptomycin; antifungal agents such as amphotericin B, caspofungin, clotrimazole, fluconazole, itraconazole, ketoconazole, voriconazole, terbinafine and nystatin; anti-malarial agents such as chloroquine, atovaquone, mefloquine, primaquine, quinidine and quinine; anti-mycobacterium agents such as ethambutol, isoniazid, pyrazinamide, rifampin and rifabutin; anti-parasitic agents such as albendazole, mebendazole, thiobendazole, metronidazole, pyrantel, atovaquone, iodoquinaol, ivermectin, paromycin, praziquantel, and trimatrexate; other anti-viral agents, including anti-CMV or anti-herpetic agents such as acyclovir, cidofovir, famciclovir, gangciclovir, valacyclovir, valganciclovir, vidarabine, trifluridine and foscarnet; protease inhibitors such as ritonavir, saquinavir, lopinavir, indinavir, atazanavir, amprenavir and nelfinavir; nucleotide/nucleoside/non-nucleoside reverse transcriptase inhibitors such as abacavir, ddI, 3TC, d4T, ddC, tenofovir and emtricitabine, delavirdine, efavirenz and nevirapine; other anti-viral agents such as interferons, ribavirin and trifluridiene; other anti-bacterial agents, including cabapenems like ertapenem, imipenem and meropenem; cephalosporins such as cefadroxil, cefazolin, cefdinir, cefditoren, cephalexin, cefaclor, cefepime, cefoperazone, cefotaxime, cefotetan, cefoxitin, cefpodoxime, cefprozil, ceftazidime, ceftibuten, ceftizoxime, ceftriaxone, cefuroxime and loracarbef; other macrolides and ketolides such as azithromycin, clarithromycin, dirithromycin and telithromycin; penicillins (with and without clavulanate) including amoxicillin, ampicillin, pivampicillin, dicloxacillin, nafcillin, oxacillin, piperacillin, and ticarcillin; tetracyclines such as doxycycline, minocycline and tetracycline; other anti-bacterials such as aztreonam, chloramphenicol, clindamycin, linezolid, nitrofurantoin and vancomycin; alpha blocker agents such as doxazosin, prazosin and terazosin; calcium-channel blockers such as amlodipine, bepridil, diltiazem, felodipine, isradipine, nicardipine, nifedipine, nisoldipine and verapamil; other anti-hypertensive agents such as clonidine, diazoxide, fenoldopan, hydralazine, minoxidil, nitroprusside, phenoxybenzamine, epoprostenol, tolazoline, treprostinil and nitrate-based agents; anti-coagulant agents, including heparins and heparinoids such as heparin, dalteparin, enoxaparin, tinzaparin and fondaparinux; other anti-coagulant agents such as hirudin, aprotinin, argatroban, bivalirudin, desirudin, lepirudin, warfarin and ximelagatran; anti-platelet agents such as abciximab, clopidogrel, dipyridamole, optifibatide, ticlopidine and tirofiban; prostaglandin PDE-5 inhibitors and other prostaglandin agents such as alprostadil, carboprost, sildenafil, tadalafil and vardenafil; thrombin inhibitors; antithrombogenic agents; anti-platelet aggregating agents; thrombolytic agents and/or fibrinolytic agents such as alteplase, anistreplase, reteplase, streptokinase, tenecteplase and urokinase; anti-proliferative agents such as sirolimus, tacrolimus, everolimus, zotarolimus, paclitaxel and mycophenolic acid; hormonal-related agents including levothyroxine, fluoxymestrone, methyltestosterone, nandrolone, oxandrolone, testosterone, estradiol, estrone, estropipate, clomiphene, gonadotropins, hydroxyprogesterone, levonorgestrel, medroxyprogesterone, megestrol, mifepristone, norethindrone, oxytocin, progesterone, raloxifene and tamoxifen; anti-neoplastic agents, including alkylating agents such as carmustine lomustine, melphalan, cisplatin, fluorouracil3, and procarbazine antibiotic-like agents such as bleomycin, daunorubicin, doxorubicin, idarubicin, mitomycin and plicamycin; anti proliferative agents (such as 1,3-cis retinoic acid, 5-fluorouracil, taxol, rapamycin, mitomycin C and cisplatin); antimetabolite agents such as cytarabine, fludarabine, hydroxyurea, mercaptopurine and 5-fluorouracil (5-FU); immune modulating agents such as aldesleukin, imatinib, rituximab and tositumomab; mitotic inhibitors docetaxel, etoposide, vinblastine and vincristine; radioactive agents such as strontium-89; and other anti-neoplastic agents such as irinotecan, topotecan and mitotane.

The therapeutic agents may be released or eluted from the drug delivery implant, bound to a surface of the implant, and/or disposed in the implant. The therapeutic agents may also be released from a separate drug eluting implant that is implantable in the same or a different location in the eye or orbital cavity. The separate drug eluting implant may be located in a physiologic outflow pathway or physiologic cavity of the eye or body, or may be implanted into an artificially formed site of the eye or body. A variety of controlled-release technologies may be used with the drug delivery implant, including non-degradable and biodegradable polymeric and non-polymeric release platforms that are known in the art and that which is described hereinabove including with respect to biodegradable polymers such as PLGA.

In one embodiment, an injection/infusion/implantation routes or sites include a suprachoroidal site and other sites along the uveoscleral pathway.

In some embodiments, combinations of agents having synergistic and/or complementary effects for a particular disease or set of related conditions or symptoms may be used. In one example, a disease-treating agent may be used in combination with a metabolism-altering agent affecting the cytochrome P450 system to affect the pharmacokinetics of the disease-treating agent. In another example, an anti-infective agent may be combined with an anti-inflammatory agent to treat inflammation resulting from the infection.

As is well known in the art, an implant device coated or loaded with a slow-release substance can have prolonged effects on local tissue surrounding the device. The slow-release delivery can be designed such that an effective amount of substance is released over a desired duration. "Substance," as used herein, is defined as any therapeutic or bioactive drug or agents that can stop, mitigate, slow-down or reverse undesired disease processes.

In one embodiment, the drug delivery implant may be coated, loaded or made in whole or in part of a biodegradable (also including bioerodible) material admixed or compounded with a substance for substance slow-release into ocular tissues. Accordingly, in the embodiments described herein, it is to be understood that incorporation of a therapeutic agent(s) in or on a device includes having the therapeutic agent included alone, with one or more pharmaceutically acceptable excipients, and compounded or admixed with a biodegradable polymer or other material to deliver the therapeutic agent(s) at a desired rate over time.

In another embodiment, polymer films may function as substance containing release devices whereby the polymer films may be coupled or secured to the drug delivery implant. The polymer films may be designed to permit the controlled release of the substance at a chosen rate and for a selected duration, which may also be episodic or periodic. Such polymer films may be synthesized such that the substance is bound to the surface or resides within a pore in the film so that the substance is relatively protected from enzymatic attack. The polymer films may also be modified to alter their hydrophilicity, hydrophobicity and vulnerability to platelet adhesion and enzymatic attack. In one embodiment, the polymer film is made of biodegradable material.

Furthermore, the film may be coupled (locally or remotely) to a power source such that when substance delivery is desired, a brief pulse of current is provided to alter the potential on the film to cause the release of a particular amount of the substance for a chosen duration. Application of current causes release of a substance from the surface of the film or from an interior location in the film such as within a pore. The rate of substance delivery is altered depending on the degree of substance loading on the film, the voltage applied to the film, and by modifying the chemical synthesis of substance delivery polymer film.

The power-activated substance delivery polymer film may be designed to be activated by an electromagnetic field, such as, by way of example, NMR, MRI, or short range RF transmission (such as a Bluetooth® apparatus). In addition, ultrasound can be used to cause a release of a particular amount of substance for a chosen duration. This is particularly applicable to a substance coated implant or an implant made of a substrate containing the desired substance.

The drug delivery implant can be used for a direct release of pharmaceutical preparations into ocular tissues. As discussed above, the pharmaceuticals may be compounded within the drug delivery implant or form a coating on the implant. Any known drug therapy for glaucoma may be utilized, including but not limited to, the following:

U.S. Pat. No. 6,201,001, issued Mar. 13, 2001, the entire contents of which are incorporated herein by reference, discloses Imidazole antiproliferative agents useful for neovascular glaucoma.

U.S. Pat. No. 6,228,873, issued May 8, 2001, the entire contents of which are incorporated herein by reference, discloses a new class of compounds that inhibit function of sodium chloride transport in the thick ascending limb of the loop of Henle, wherein the preferred compounds useful are furosemide, piretanide, benzmetanide, bumetanide, torasernide and derivatives thereof.

U.S. Pat. No. 6,194,415, issued Feb. 27, 2001, the entire contents of which are incorporated herein by reference, discloses a method of using quinoxalines (2-imidazolin-2-ylamino) in treating neural injuries (e.g., glaucomatous nerve damage).

U.S. Pat. No. 6,060,463, issued May 9, 2000, and U.S. Pat. No. 5,869,468, issued Feb. 9, 1999, the entire contents of which are incorporated herein by reference, disclose treatment of conditions of abnormally increased intraocular pressure by administration of phosphonylmethoxyalkyl nucleotide analogs and related nucleotide analogs.

U.S. Pat. No. 5,925,342, issued Jul. 20, 1999, the entire contents of which are incorporated herein by reference, discloses a method for reducing intraocular pressure by administration of potassium channel blockers.

U.S. Pat. No. 5,814,620, issued Sep. 29, 1998, the entire contents of which are incorporated herein by reference, discloses a method of reducing neovascularization and of treating various disorders associated with neovascularization. These methods include administering to a tissue or subject a synthetic oligonucleotide.

U.S. Pat. No. 5,767,079, issued Jun. 16, 1998, the entire contents of which are incorporated herein by reference, discloses a method for treatment of ophthalmic disorders by applying an effective amount of Transforming Growth Factor-Beta (TGF-beta) to the affected region.

U.S. Pat. No. 5,663,205, issued Sep. 2, 1997, the entire contents of which are incorporated herein by reference, discloses a pharmaceutical composition for use in glaucoma treatment which contains an active ingredient 5-[1-hydroxy-2-[2-(2-methoxyphenoxy)ethylamino]ethyl]-2-methylbenzenesulfonamide. This agent is free from side effects, and stable and has an excellent intraocular pressure reducing activity at its low concentrations, thus being useful as a pharmaceutical composition for use in glaucoma treatment.

U.S. Pat. No. 5,652,236, issued Jul. 29, 1997, the entire contents of which are incorporated herein by reference, discloses pharmaceutical compositions and a method for treating glaucoma and/or ocular hypertension in the mammalian eye by administering thereto a pharmaceutical composition which contains as the active ingredient one or more compounds having guanylate cyclase inhibition activity. Examples of guanylate cyclase inhibitors utilized in the pharmaceutical composition and method of treatment are methylene blue, butylated hydroxyanisole and N-methylhydroxylamine.

U.S. Pat. No. 5,547,993, issued Aug. 20, 1996, the entire contents of which are incorporated herein by reference, discloses that 2-(4-methylaminobutoxy) diphenylmethane or a hydrate or pharmaceutically acceptable salt thereof have been found useful for treating glaucoma.

U.S. Pat. No. 5,502,052, issued Mar. 26, 1996, the entire contents of which are incorporated herein by reference, discloses use of a combination of apraclonidine and timolol to control intraocular pressure. The compositions contain a combination of an alpha-2 agonist (e.g., para-amino clonidine) and a beta blocker (e.g., betaxolol).

U.S. Pat. No. 6,184,250, issued Feb. 6, 2001, the entire contents of which are incorporated herein by reference, discloses use of cloprostenol and fluprostenol analogues to treat glaucoma and ocular hypertension. The method comprises topically administering to an affected eye a composition comprising a therapeutically effective amount of a combination of a first compound selected from the group consisting of beta-blockers, carbonic anhydrase inhibitors, adrenergic agonists, and cholinergic agonists, together with a second compound.

U.S. Pat. No. 6,159,458, issued Dec. 12, 2000, the entire contents of which are incorporated herein by reference, discloses an ophthalmic composition that provides sustained release of a water soluble medicament formed by comprising a cross-linked carboxy-containing polymer, a medicament, a sugar and water.

U.S. Pat. No. 6,110,912, issued Aug. 29, 2000, the entire contents of which are incorporated herein by reference, discloses methods for the treatment of glaucoma by administering an ophthalmic preparation comprising an effective amount of a non-corneotoxic serine-threonine kinase inhibitor, thereby enhancing aqueous outflow in the eye and treatment of the glaucoma. In some embodiments, the method of administration is topical, whereas it is intracameral in other embodiments. In still further embodiments, the method of administration is intracanalicular.

U.S. Pat. No. 6,177,427, issued Jan. 23, 2001, the entire contents of which are incorporated herein by reference, discloses compositions of non-steroidal glucocorticoid antagonists for treating glaucoma or ocular hypertension.

U.S. Pat. No. 5,952,378, issued Sep. 14, 1999, the entire contents of which are incorporated herein by reference, discloses the use of prostaglandins for enhancing the delivery of drugs through the uveoscleral route to the optic nerve head for treatment of glaucoma or other diseases of the optic nerve as well as surrounding tissue. The method for enhancing the delivery to the optic nerve head comprises contacting a therapeutically effective amount of a composition containing one or more prostaglandins and one or more drug substances with the eye at certain intervals.

Drug Delivery Implants

Figure 2A:
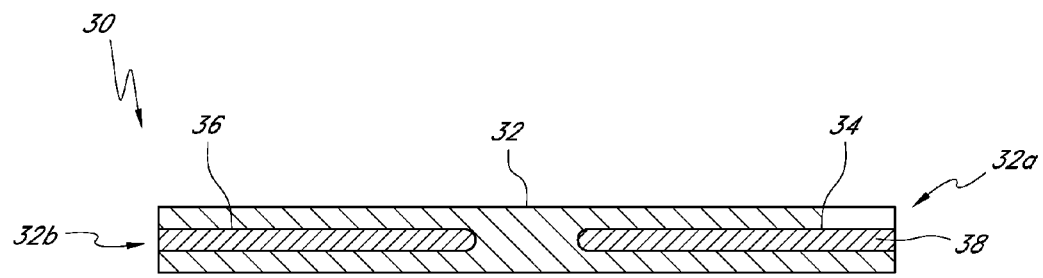
FIG. 2A is a longitudinal cross-section of one embodiment of a drug delivery implant.
Figure 2B:
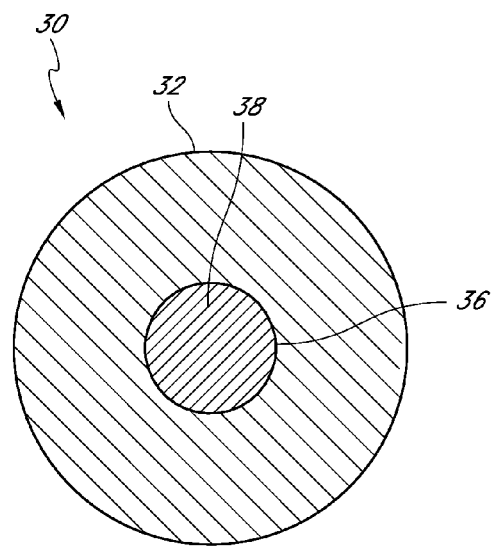
FIG. 2B is a transverse cross-section of the drug delivery implant of FIG. 2A.

Embodiment Illustrated in FIGS. 2A-2B

FIGS. 2A-2B show one embodiment of a drug delivery implant 30. The drug delivery implant 30 can have an elongated body 32 extending from a proximal end 32a to a distal end 32b that in one embodiment can be generally cylindrical with a circular cross-section. However, in other embodiments the elongated body 32 can have other cross-sectional shapes, such as a semi-sphere, a paraboloid, or a hyperboloid.

The drug delivery implant 30 preferably has an outer diameter that will permit the implant 30 to fit within a 21-gauge or 23-gauge needle or hollow instrument during implantation; however, larger or smaller gauge instruments can also be used. The implant 30 can also have a diameter that is designed to be delivered with larger needles. For example, the implant 30 can also be delivered with 18-, 19- or 20-gauge needles. The implant 30 can have a constant diameter through most of the length of the implant 30, or the implant 30 can have portions of reduced diameter, e.g., annular grooves (not shown), between the proximal end 32a and the distal end 32b. The annular grooves can produce an irregular outer surface on the body 32 that can operate to mechanically lock or anchor the implant 30 in place when implanted. Of course, such surface discontinuities or irregularities can also be formed by barbs or other projections, which extend from the outer surface of the implant 30, to inhibit migration of the implant 30 from its implanted position, as described above.

In one embodiment, at least one of the proximal and distal ends, 32a, 32b can include a tapered portion. During implantation, the tapered end can operate to form, dilate, and/or increase the size of, an incision or puncture created in the tissue. For example, the distal end 32b can operate as a trocar to puncture or create an incision in the tissue. Following advancement of the distal end 32b of the implant 30, the tapered portion can be advanced through the puncture or incision. The tapered portion can operate to stretch or expand the tissue around the puncture or incision to accommodate the increasing size of the tapered portion as it is advanced through the tissue. The interaction of the tissue and the edges of the implant 30 will provide an anchor for the implant 30 following implantation to inhibit migration of the drug delivery implant 30.

The tapered portion can also facilitate proper location of the drug delivery implant 30 into the supraciliary or suprachoroidal spaces. For example, the implant 30 is preferably advanced through the tissue within the anterior chamber angle during implantation. This tissue typically is fibrous or porous, which is relatively easy to pierce or cut with a surgical device, such as the tip of the implant 30. The implant 30 can be advanced through this tissue and abut against the sclera once the implant 30 extends into the uveoscleral outflow pathway. As the implant 30 abuts against the sclera, the tapered portion can preferably provide a generally rounded edge or surface that facilitates sliding of the implant 30 within the suprachoroidal space along the interior wall of the sclera 11. For example, as the implant 30 is advanced into the uveoscleral outflow pathway and against the sclera 11, the implant 30 will likely be oriented at an angle with respect to the interior wall of the sclera 11. As the tip of the implant 30 engages the sclera 11, the tip preferably has a radius that will permit the implant 30 to slide along the sclera 11 instead of piercing or substantially penetrating the sclera 11. As the implant 30 slides along the sclera 11, the tapered portion will provide an edge against which the implant 30 can abut against the sclera 11 and reduce the likelihood that the drug delivery implant 30 will pierce the sclera.

In one embodiment, once the implant 30 is implanted in position, the distal portion 32b can reside in the anterior chamber 20 and the proximal portion 32a can reside in the suprachoroidal space 24 of the uveoscleral outflow pathway 24a.

The implant 30 preferably comprises any of the materials previously described above. The implant 30 can be fabricated through micro machining techniques or through procedures commonly used for fabricating optical fibers. For example, in some embodiments, the implant 30 is drawn with a recess extending therethrough. In the illustrated embodiment, the drug delivery implant 30 includes a first elongated recess 34 extending along an axis of the implant body 32 from the proximal end 32a of the implant 30, and a second elongated recess 36 extending along the axis of the implant body 32 from the distal end of the implant 30. In one embodiment a therapeutic agent 38, as described herein, can be disposed in the recesses 34, 36 of the drug delivery implant 30.

In one embodiment, the drug delivery implant 30 can be implanted in the uveoscleral outflow pathway 24a such that the proximal portion 32a is in the suprachoroidal space 24 and the distal portion 32b is near the anterior chamber 20, so that the therapeutic agent 38 in the implant 30 can be delivered to both the suprachoroidal space 24 and the anterior chamber 20. In one embodiment, the same therapeutic agent 38 can be disposed in the recesses 34, 36. In another embodiment, the therapeutic agents 38 in the recesses 34, 36 can be different so as to provide different therapies to the anterior chamber 20 and the suprachoroidal space 24.

Figure 3:
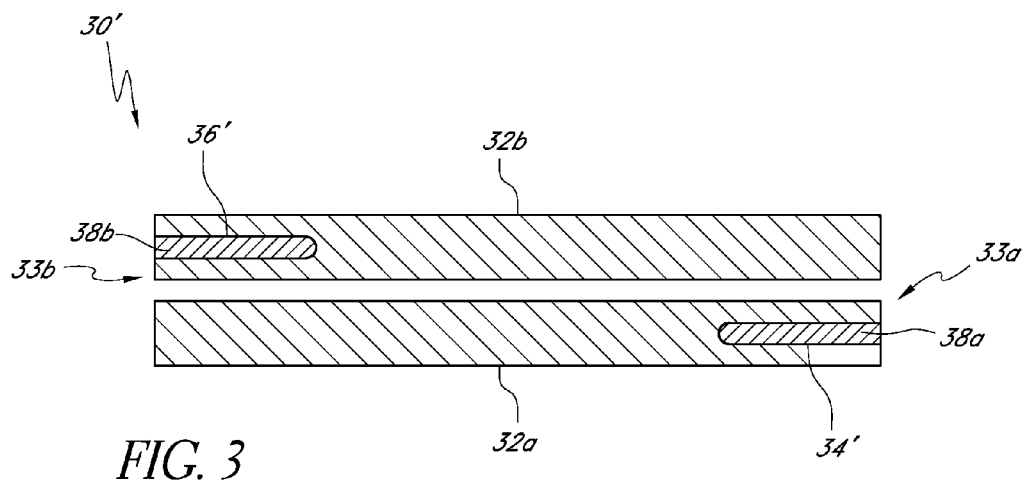
FIG. 3 is a longitudinal cross-section of another embodiment of a drug delivery implant.

Embodiment Illustrated in FIG. 3

FIG. 3 shows another embodiment of a drug delivery implant 30'. The drug delivery implant 30' is similar to the drug delivery implant 30 of FIGS. 2A-2B, except as noted below. Thus, the reference numerals used to designate the various features of the drug delivery implant 30' are identical to those used for identifying the corresponding features of the drug delivery implant 30, except that a "'" has been added to the reference numerals.

The drug delivery implant 30' includes a first elongated body 32a with a recess 34' at a proximal end 33a thereof that can have a therapeutic agent 38a therein. The drug delivery implant 30' also includes a second elongated body 32b with a recess 36' at a distal end 33b thereof that can include a therapeutic agent 38b therein. In one embodiment, the therapeutic agents 38a, 38b are the same. In another embodiment, the therapeutic agents 38a, 38b are different.

Preferably, the first and second elongated bodies 32a, 32b have the same length and can couple to each other along their lengths so that the first and second elongated bodies 32a, 32b can define a unitary body. For example, the first and second elongated bodies 32a, 32b can define an interlocking mechanism on at least a portion of their respective outer surfaces (e.g., interlocking key and groove features) to allow for said coupling of the elongated bodies 32a, 32b. In one embodiment, the elongated bodies 32a, 32b can be delivered sequentially to the implantation site and coupled together following implantation. In another embodiment, the elongated bodies 32a, 32b can be coupled prior to implantation and delivered to the implantation site as a unitary body. In one embodiment, the first and second elongated bodies 32a, 32b can be oriented so that the therapeutic agents 38a, 38b are directed in opposite directions (e.g., one toward the anterior chamber 20 and the second toward the suprachoroidal space 24). In another embodiment, the first and second elongated bodies 32a, 32b can be oriented so that the therapeutic agents 38a, 38b are directed in the same direction.

Figure 4A:
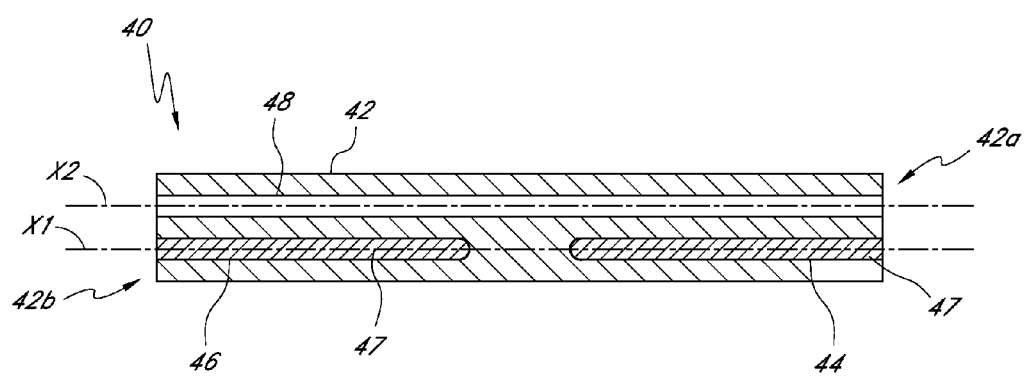
FIG. 4A is a longitudinal cross-section of another embodiment of a drug delivery implant.
Figure 4B:
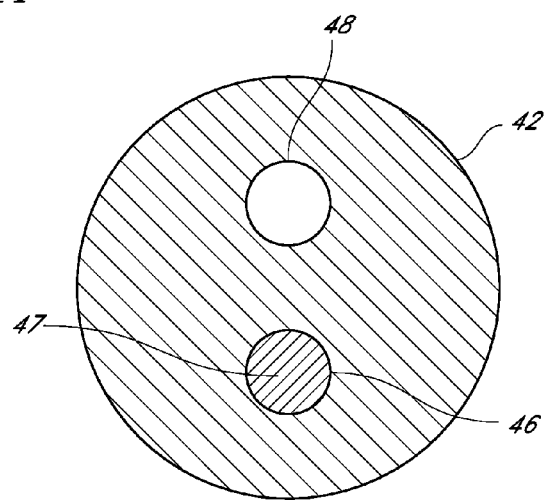
FIG. 4B is a transverse cross-section of the drug delivery implant of FIG. 4A.

Embodiment Illustrated in FIGS. 4A-4B

FIGS. 4A-4B illustrate another embodiment of a drug delivery implant 40. The drug delivery implant 40 is similar to the drug delivery implant 30 of FIGS. 2A-2B, except as noted below.

The drug delivery implant 40 includes an elongated body 42 that can extend along an axis between a proximal end 42a and a distal end 42b. The implant 40 can include a first recess 44 at the proximal end 42a thereof and a second recess 46 at the distal end 42b thereof, where each of the recesses 44, 46 can have a therapeutic agent 47 therein. In the illustrated embodiment, the recesses 44, 46 are aligned along a first axis X1.

The drug delivery implant 40 also defines a shunt with a lumen 48 that extends through the implant 40 along a second axis X2 generally parallel to the first axis X1. Preferably, the lumen 48 is sized to allow flow of aqueous humor therethrough. In one embodiment, where the drug delivery implant 40 is implanted in the uveoscleral outflow pathway 24a so that the proximal end 42a is oriented toward the suprachoroidal space 24 and the distal end 42b is directed toward the anterior chamber 20, the lumen 48 preferably enhances the drainage of aqueous humor from the anterior chamber 20 to the suprachoroidal space 24 via the implant 40.

The flow of fluid is preferably restricted by the size of the lumen 48, which produces a capillary effect that limits the fluid flow for given pressures. The capillary effect of the lumen 48 allows the shunt of the implant 40 to restrict flow and provides a valveless regulation of fluid flow. The flow of fluid through the implant 40 is preferably configured to be restricted to flow rated that will reduce the likelihood of hypotony in the eye. For example, in some embodiments, the flow rate can be limited to about 2.5 µL/min or less. In some embodiments the flow rate can be limited to between about 1.9 µL/min and about 3.1 µL/min. In other applications, a plurality of drug delivery implants 40 can be used in a single eye to conduct fluid from the anterior chamber to the uveoscleral outflow pathway. In such applications, the cumulative flow rate through the shunts of the implants 40 preferably is within the range of about 1.9 µL/min to about 3.1 µL/min, although the flow rate for each of the shunts of the implants 40 can be significantly less than about 2.5 µL/min. For example, if an application called for implantation of five shunts, then each implant 40 can be configured to have a flow rate of about 0.5 µL/min.

In the illustrated embodiment, the lumen 48 of the implant 40 is depicted as extending along the axis X2 and offset from the longitudinal center of the implant 40. In another embodiment, the lumen 48 can extend along the longitudinal center of the implant 40. Additionally, the lumen 48 can vary in direction along its length. Also, though the illustrated embodiment shows the lumen 48 having a generally straight configuration between the proximal and distal ends 42a, 42b of the implant, in one embodiment the lumen 48 can have a non-linear (e.g., spiral) configuration. In the illustrated embodiment, the lumen 48 has a generally constant diameter from the proximal to the distal ends 42a, 42b. In another embodiment, the diameter of the lumen 48 can vary (e.g., taper) along its length, or there can be a discontinuity in the diameter of the lumen 48 at a location along its length (e.g., to control the flow rate of aqueous humor therethrough).

The drug delivery implant 40 can be of any of the materials described herein. The implant 40 can be fabricated through conventional micro machining techniques or through procedures commonly used for fabricating optical fibers. Other materials can be used for the implant 40, and other methods of manufacturing the implant 40 can also be used. For example, the implant 40 can be constructed of metals or plastics, and the implant 40 can be machined with a bore that is drilled as described above.

Figure 5:
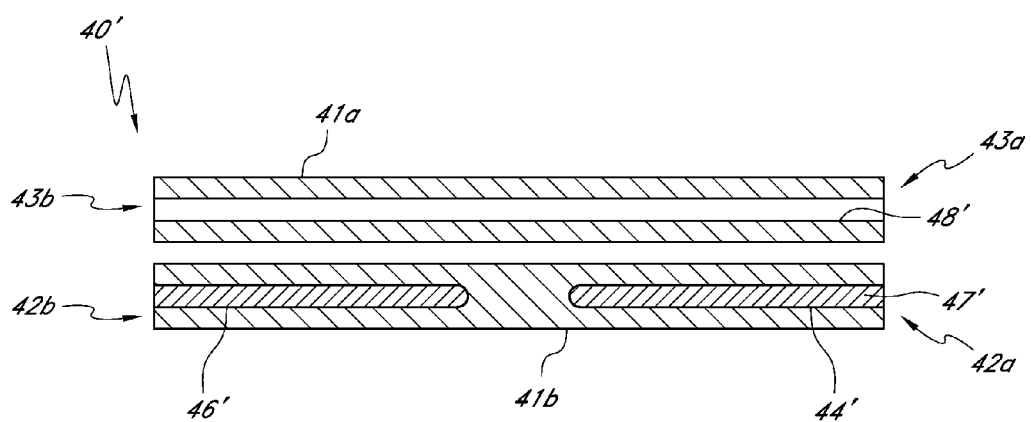
FIG. 5 is a longitudinal cross-section of another embodiment of a drug delivery implant.

Embodiment Illustrated in FIG. 5

FIG. 5 illustrates another embodiment of a drug delivery implant 40'. The drug delivery implant 40' is similar to the drug delivery implant 40 of FIGS. 4A-4B, except as noted below. Thus, the reference numerals used to designate the various features of the drug delivery implant 40' are identical to those used for identifying the corresponding features of the drug delivery implant 40, except that a "'" has been added to the reference numerals.

In the illustrated embodiment, the drug delivery implant 40' has a lumen 48' that extends between a proximal end 43a and a distal end 43b of an elongated body 41a (e.g., shunt) that is separate from an elongated body 41b that includes the recesses 44', 46' and therapeutic agent 47'. The recesses 44', 46' extend along the central axis of the elongated body 41b and the lumen 48 extends along the central axis of the elongated body 41a.

Preferably, the first and second elongated bodies 41a, 41b have the same length and can couple to each other along their lengths, prior to or following implantation, so that the first and second elongated bodies 41a, 41b can define a unitary body. For example, the first and second elongated bodies 41a, 41b can define an interlocking mechanism, as discussed above, on at least a portion of their respective outer surfaces (e.g., interlocking key and groove features) to allow for said coupling of the elongated bodies 41a, 41b. In one embodiment, the elongated bodies 41a, 41b can be delivered sequentially to the implantation site and coupled together following implantation. In another embodiment, the elongated bodies 41a, 41b can be coupled prior to implantation and delivered to the implantation site as a unitary body.

Figure 6:
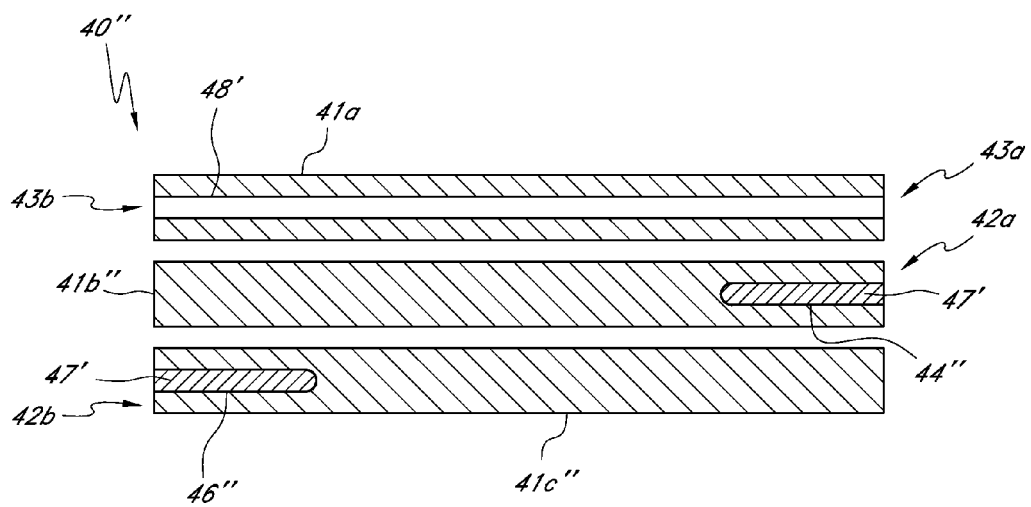
FIG. 6 is a longitudinal cross-section of another embodiment of a drug delivery implant.

Embodiment Illustrated in FIG. 6

FIG. 6 illustrates another embodiment of a drug delivery implant 40". The drug delivery implant 40" is similar to the drug delivery implant 40' of FIG. 5, except as noted below. Thus, the reference numerals used to designate the various features of the drug delivery implant 40" are identical to those used for identifying the corresponding features of the drug delivery implant 40', except that a "'"" has been added to the reference numerals.

In the illustrated embodiment, the drug delivery implant 40" includes a shunt 41a that defines the lumen 48', a first elongated body 41b" that has a recess 44" at a proximal end 42a thereof, and a second elongated body 41c" that has a recess 46" at a distal end 42b thereof, where the therapeutic agent 47' can be disposed in the recesses 44", 46". In one embodiment, the lumen 48', recess 44" and recess 46" can extend along the central axes of the shunt 41a, first elongated body 41b" and second elongated boy 41c", respectively.

Preferably, at least two of the shunt 41a and first and second elongated bodies 41b", 41c" have the same length and can be coupled to each other along their lengths (e.g., via an interlocking mechanism defined on their outer surfaces) so as to define a unitary body. In one embodiment, the shunt 41a and first and second elongated bodies 41b", 41c"can be delivered sequentially to the implantation site and coupled together following implantation. In another embodiment, the shunt 41a and first and second elongated bodies 41b", 41c" can be coupled prior to implantation and delivered to the implantation site as a unitary body. The first and second elongated bodies 41b", 41c" can be oriented so that the therapeutic agents 47' are directed in opposite directions (e.g., one toward the anterior chamber 20 and the second toward the suprachoroidal space 24). In another embodiment, the first and second elongated bodies 41b", 41c" can be oriented so that the therapeutic agents 47' are directed in the same direction.

Figure 7:
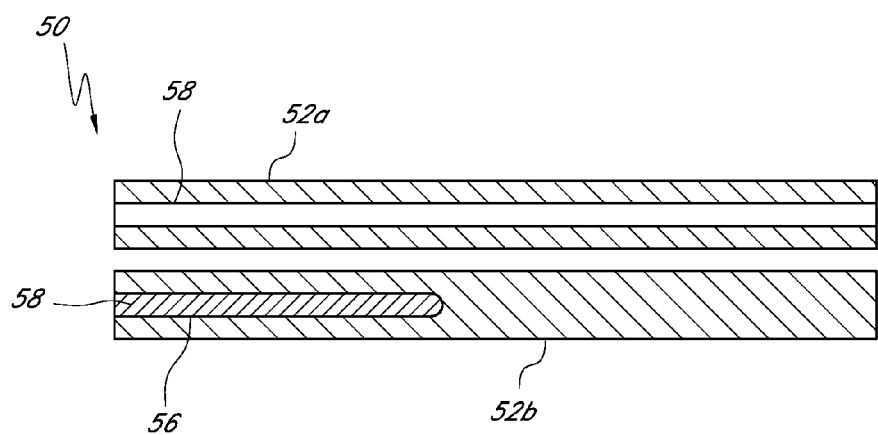
FIG. 7 is a longitudinal cross-section of another embodiment of a drug delivery implant.

Embodiment Illustrated in FIG. 7

FIG. 7 illustrates another embodiment of a drug delivery implant 50. In the illustrated embodiment, the drug delivery implant 50 includes a shunt 52a that defines a lumen 58 therethrough, and a first elongated body 52b that has a recess 56 at one end thereof, where a therapeutic agent 57 can be disposed in the recess 56. In one embodiment, the lumen 58 and recess 56 can extend along the central axes of the shunt 52a and elongated body 52b, respectively. The lumen 58 can be generally linear in one embodiment. In another embodiment, the lumen 58 can be non-linear.

Preferably, the shunt 52a and elongated body 52b have the same length and can be coupled to each other along their lengths (e.g., via an interlocking mechanism defined on their outer surfaces) so as to define a unitary body, prior to or following implantation.

Figure 8A:
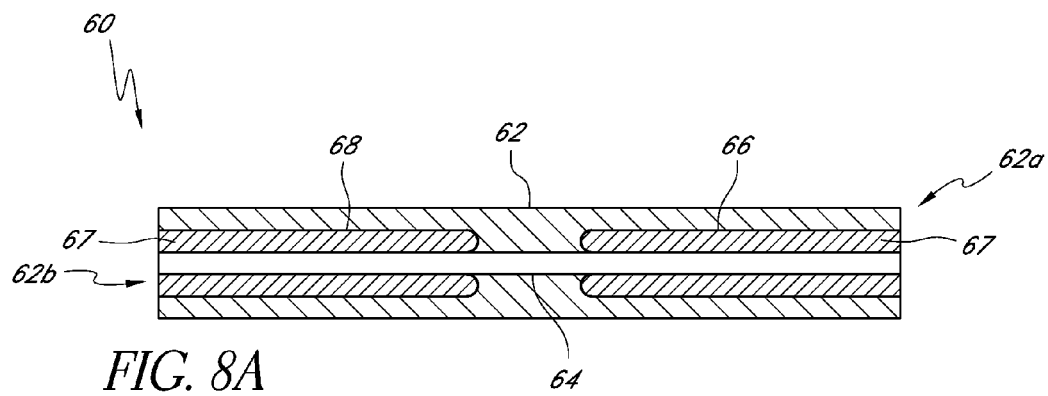
FIG. 8A is a longitudinal cross-section of another embodiment of a drug delivery implant.
Figure 8B:
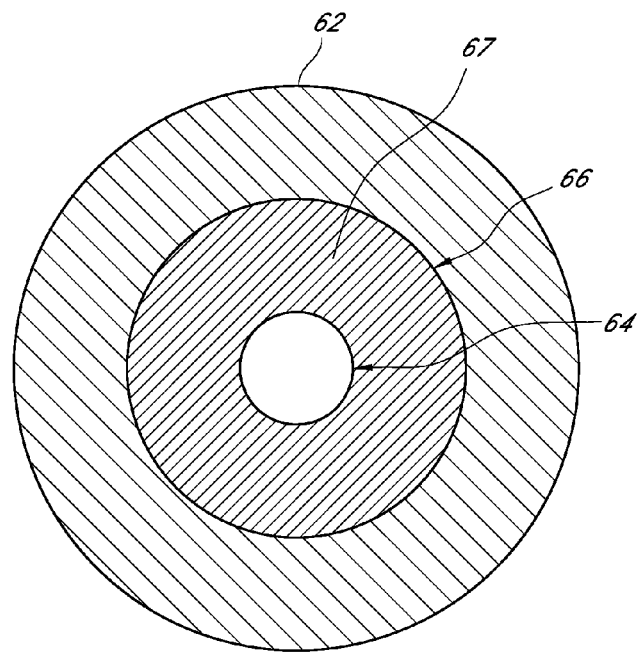
FIG. 8B is a transverse cross-section of the drug delivery implant of FIG. 8A.

Embodiment Illustrated in FIGS. 8A-8B

FIGS. 8A-8B illustrates another embodiment of a drug delivery implant 60. In the illustrated embodiment, the drug delivery implant 60 includes an elongate body 62 that extends between a proximal end 62a and a distal end 62b and defines a lumen 64 that extends though the elongate body 62. In the illustrate embodiment, the lumen 64 extends along a central axis of the elongate body 62. However, in another embodiment, the lumen 64 can extend along an axis offset from the central axis of the body 62. The lumen 64 can be generally linear. In another embodiment, the lumen 64 can be non-linear.

The drug delivery implant 60 also includes a first recesses 66 formed in the proximal portion 62a of the elongate body 62 about the lumen 64. The drug delivery implant 60 also includes a second recesses 68 formed in the distal portion 62b of the elongate body 62 about the lumen 64. The drug delivery implant 60 also includes a therapeutic agent 67 that can be disposed in the recesses 66, 68. In one embodiment, the therapeutic agent 67 in the recesses 66, 68 can be the same. In another embodiment, the therapeutic agent 67 in the recesses 66, 68 can be different.

Advantageously, the drug delivery implant 60 allows for fluid flow therethrough via the lumen 64, and said fluid flow is exposed to the therapeutic agent 67 and can carry it to a desired location. Where the implant 60 is implanted in the uveoscleral outflow pathway 24a so that the proximal end 62a is oriented toward the suprachoroidal space 24 and the distal end 62b is oriented toward the anterior chamber 20, the lumen 64 allows for aqueous humor to flow from the anterior chamber 20, through the elongate body 62 where the therapeutic agent 67 enters the fluid stream, and toward the suprachoroidal space 24.

In one embodiment, the recesses 66, 68 can be circumferential recesses formed in the proximal and distal portions 62a, 62b of the elongate body 62, respectively. In another embodiment, the recesses 66, 68 can each include two separate and distinct recesses at the formed in the elongate body 62 on radially opposite sides of the lumen 64. In another embodiment, the drug delivery implant 60 can include only one circumferential recess at a proximal portion, distal portion, or central portion of the elongate body 62.

Figure 9A:
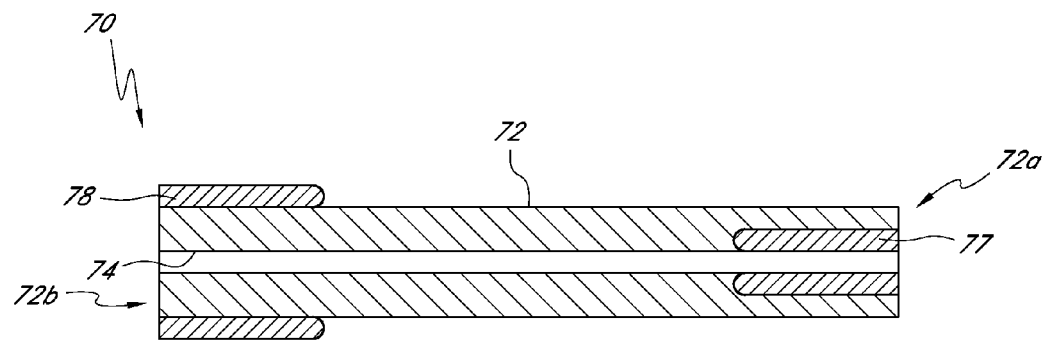
FIG. 9A is a longitudinal cross-section of another embodiment of a drug delivery implant.
Figure 9B:
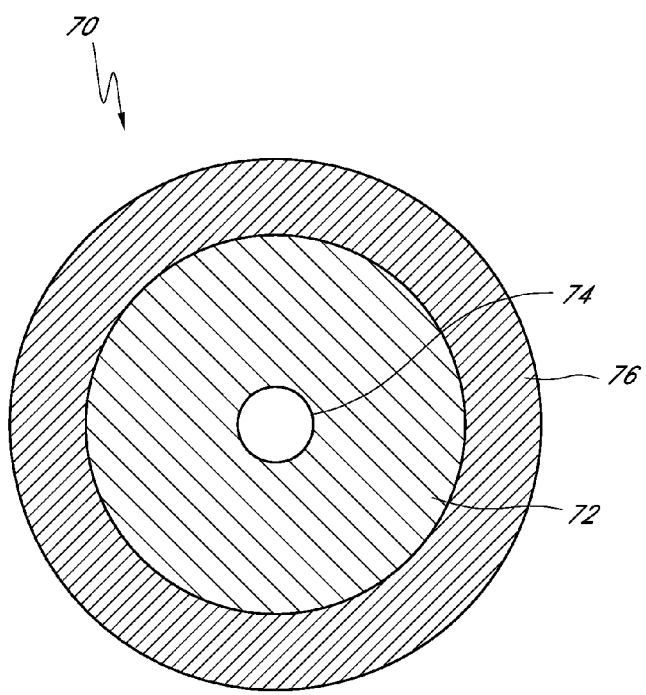
FIG. 9B is a transverse cross-section of the drug delivery implant of FIG. 9A.

Embodiment Illustrated in FIGS. 9A-9B

FIGS. 9A-9B illustrate another embodiment of a drug delivery implant 70. In the illustrated embodiment, the drug delivery implant 70 includes an elongate body 72 that extends between a proximal end 72a and a distal end 72b and defines a lumen 74 that extends though the elongate body 72. In the illustrate embodiment, the lumen 74 extends along a central axis of the elongate body 72. However, in another embodiment, the lumen 74 can extend along an axis offset from the central axis of the body 72. The lumen 74 can be generally linear. In another embodiment, the lumen 74 can be non-linear.

The drug delivery implant 70 also includes a recesses 76 formed in the proximal portion 72a of the elongate body 72 about the lumen 74. The drug delivery implant 70 also includes a first therapeutic agent 77 that can be disposed in the recess 76 and a second therapeutic agent 78 that can be disposed on an outer surface of the elongate body 72 at the distal portion 72b thereof. In one embodiment, the therapeutic agent 78 can be a film or a coating applied to the outer surface of the elongate body 72. In one embodiment, the therapeutic agents 77, 78 are the same. In another embodiment, the therapeutic agent 78 can be different from the therapeutic agent 77.

Advantageously, the drug delivery implant 70 allows for fluid to flow therethrough via the lumen 74, and said fluid flow is exposed to the therapeutic agent 77 and can carry it to a desired location. Additionally, ocular tissue surrounding the drug delivery implant 70 can be exposed to the therapeutic agent 78 on the outer surface of the elongate body 72. Where the implant 70 is implanted in the uveoscleral outflow pathway 24a so that the proximal end 72a is oriented toward the suprachoroidal space 24 and the distal end 72b is oriented toward the anterior chamber 20, the lumen 74 allows for aqueous humor to flow from the anterior chamber 20, through the elongate body 72 where the therapeutic agent 77 enters the fluid stream, and toward the suprachoroidal space 24.

In one embodiment (not shown), the recess 76 can extend along the length of the elongate body 72 about the lumen 74. In another embodiment, the recess 76 can include two separate and distinct recesses at the formed in the elongate body 72 on radially opposite sides of the lumen 74. In another embodiment, the recess 76 can be located at a proximal portion, distal portion, or central portion of the elongate body 72. Additionally, in one embodiment, the second therapeutic agent 78 can be disposed on the outer surface of the drug delivery implant 70 along the entire length of the elongate body 72.

Figure 10:
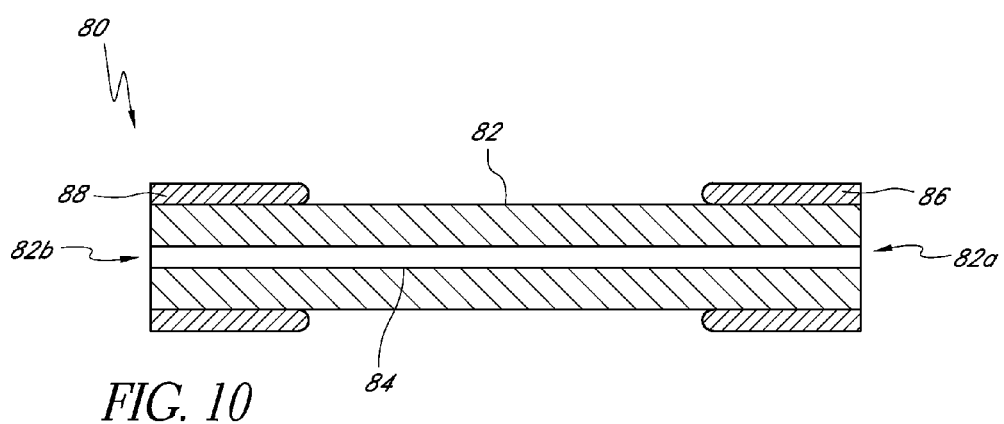
FIG. 10 is a longitudinal cross-section of another embodiment of a drug delivery implant.
Figure 11B:
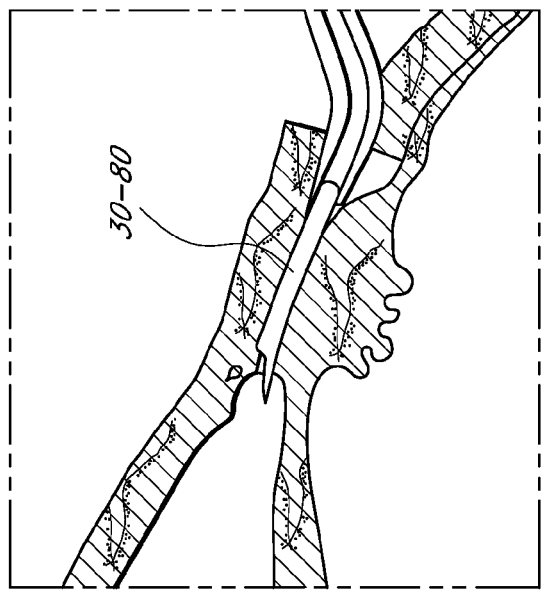
FIG. 11B is an enlarged cross-sectional detailed view of FIG. 11A.
Figure 11A:
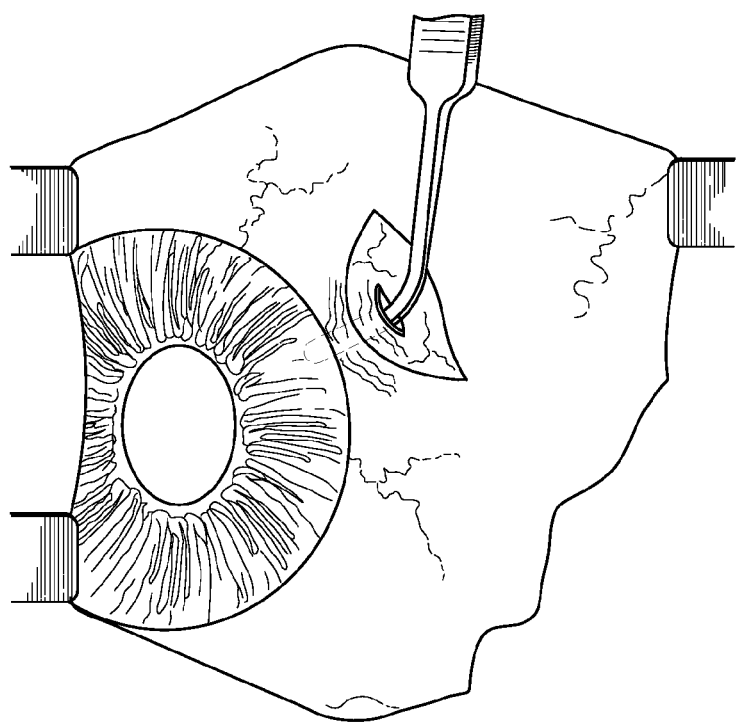
FIG. 11A is a partial top view of an eye showing one embodiment of a method for implantation of a drug delivery implant into the eye.
Figure 12B:
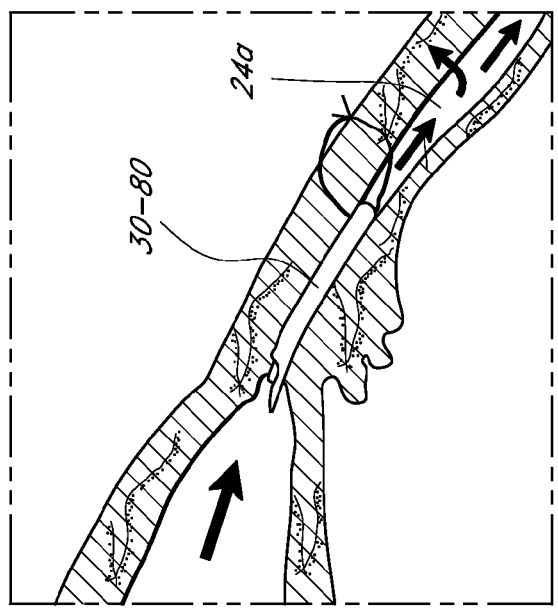
FIG. 12B is an enlarged cross-sectional detailed view of the implant in FIG. 12A.
Figure 12A:
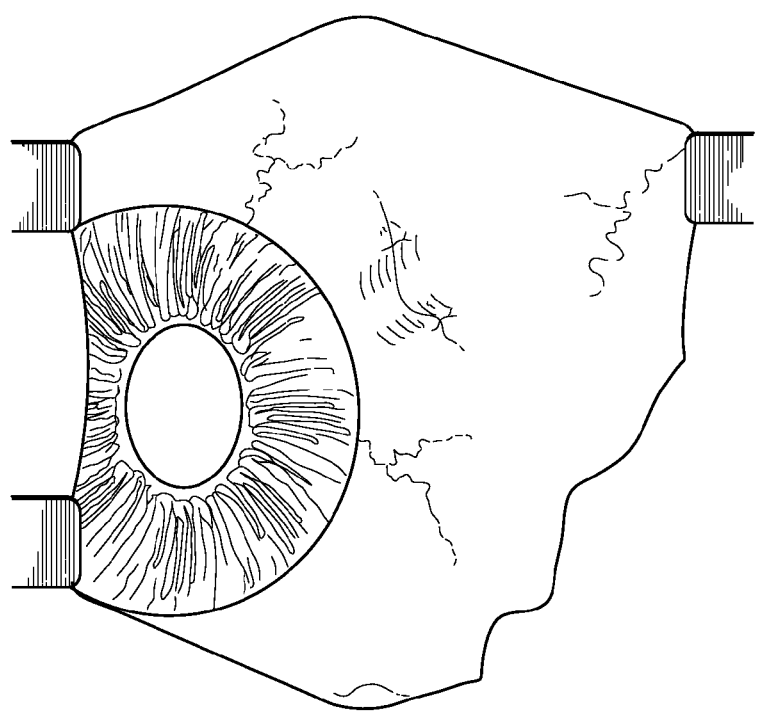
FIG. 12A is a partial top view of an eye into which a drug delivery implant has been implanted.

Embodiment Illustrated in FIG. 10

FIG. 10 illustrates another embodiment of a drug delivery implant 80. In the illustrated embodiment, the drug delivery implant 80 includes an elongate body 82 that extends between a proximal end 82a and a distal end 82b and defines a lumen 84 that extends though the elongate body 82. In the illustrate embodiment, the lumen 84 extends along a central axis of the elongate body 82. However, in another embodiment, the lumen 84 can extend along an axis offset from the central axis of the body 82. The lumen 84 can be generally linear. In another embodiment, the lumen 84 can be non-linear.

The drug delivery implant 80 also includes a first therapeutic agent 86 that can be disposed on the outer surface of the proximal portion 82a of the elongate body 82 and a second therapeutic agent 88 that can be disposed on an outer surface of the elongate body 82 at the distal portion 82b thereof. The therapeutic agents 86, 88 can be a film or a coating applied to the outer surface of the elongate body 82. In one embodiment, the therapeutic agents 86, 88 are the same. In another embodiment, the therapeutic agent 86 can be different from the therapeutic agent 88.

In the illustrated embodiment, the therapeutic agents 86, 88 extend circumferentially about the elongate body 82. In another embodiment, the discreet portions of the therapeutic agents 86, 88 can be disposed on the elongate body 82 at diametrically opposite locations.

Advantageously, ocular tissue surrounding the drug delivery implant 80 can be exposed to the therapeutic agents 86, 88 on the outer surface of the elongate body 82. Where the implant 80 is implanted in the uveoscleral outflow pathway 24a so that the proximal end 82a is oriented toward the suprachoroidal space 24 and the distal end 82b is oriented toward the anterior chamber 20, the lumen 84 allows for aqueous humor to flow from the anterior chamber 20, through the elongate body 82 and toward the suprachoroidal space 24. Additionally, scleral, choroidal and/or ciliary tissue can be exposed to the therapeutic agents 86, 88 on the drug delivery implant 80.

The drug delivery implant described in embodiments herein can be constructed of metals or plastics, or other suitable materials for implantation in ocular tissue. The drug delivery implant also need not have a unitary configuration; that is, be formed of the same material. For example, a portion of the drug delivery implant can be formed of a first material and another portion of the drug delivery implant can be formed of a second different material.

Procedures

For delivery of some embodiments of the ocular drug delivery implant, the implantation occurs in a closed chamber with or without viscoelastic.

The drug delivery implants may be placed using an applicator, such as a pusher, or they may be placed using a delivery instrument having energy stored in the instrument, such as disclosed in U.S. Patent Publication 2004/0050392, filed Aug. 28, 2002, the entirety of which is incorporated herein by reference and made a part of this specification and disclosure. In some embodiments, fluid may be infused through the delivery instrument or another instrument used in the procedure to create an elevated fluid pressure at the distal end of the shunt to ease implantation.

FIGS. 11A-12B illustrate one embodiment of a surgical method for implanting the drug delivery implant into an eye, as described in the embodiments herein. A first incision or slit is made through the conjunctiva and the sclera 11 at a location rearward of the limbus 21, that is, posterior to the region of the sclera 11 at which the opaque white sclera 11 starts to become clear cornea 12. Preferably, the first incision is made about 3 mm posterior to the limbus 21. Also, the first incision is made slightly larger than the width of the drug delivery implant. In one embodiment, a conventional cyclodialysis spatula may be inserted through the first incision into the supraciliary space to confirm correct anatomic position.

A portion of the upper and lower surfaces of the drug delivery implant proximate the back end of the body can be grasped securely by the surgical tool, for example, a forceps, so that the forward end of the implant is oriented properly. In one embodiment, the implant is oriented with a longitudinal axis of the implant being substantially co-axial to a longitudinal axis of the grasping end of the surgical tool. The drug delivery implant can then be disposed through the first incision and into the supraciliary space of the eye. In one embodiment, the drug delivery implant can have a shearing edge that can be advanced anteriorly in the supraciliary space and inserted into and through the anterior chamber angle of the eye. More particularly, the shearing edge of the insertion head of the implant can preferably pass between the scleral spur and the ciliary body 16 posterior to the trabecular meshwork. The drug delivery implant can be continually advanced anteriorly until a portion of its insertion head and the first end of the conduit is disposed within the anterior chamber 20 of the eye. Thus, the first end of the conduit is placed into fluid communication with the anterior chamber 20 of the eye. A back end of the elongate body of the drug delivery implant can be disposed into the suprachoroidal space 24 of the eye so that the second end of the conduit is placed into fluid communication with the suprachoroidal space 24.

In the illustrated embodiment, a shoulder surface of the forward end of the drug delivery implant can be seated proximate an interior surface of the supraciliary space and is not introduced into the anterior chamber 20. The shoulder surface advantageously aids in forming a tight seal to inhibit leakage of aqueous humor around the implant body as well as inhibit unwanted further anterior movement of the implant. In one embodiment, the shape of a cleft formed by the insertion head forms a tight seal about the exterior surface of the implant body, and, if used, the fusiform cross-sectional shape of the body inhibits gaping of the formed cleft on either elongate edge of the implant.

In one embodiment, the drug delivery implant can be sutured to a portion of the sclera 11 to aid in fixating the implant. In one embodiment, the first incision can subsequently be sutured closed. As one will appreciate, the suture used to fixate the drug delivery implant can also be used to close the first incision. In another embodiment, the drug delivery implant held substantially in place via the interaction of the implant body's outer surface and the tissue of the sclera 11 and ciliary body 16 without suturing the implant to the sclera 11. Additionally, in one embodiment, the first incision can be sufficiently small so that the incision self-seals upon withdrawal of the surgical tool following implantation of the drug delivery implant without suturing the incision.

As discussed herein, in some embodiments the drug delivery implant can include a shunt comprising a lumen configured provide a drainage device between the anterior chamber 20 and the suprachoroidal space 24. Upon implantation, the drainage device can form a cyclodialysis with the implant providing transverse communication of aqueous humor through the shunt along its length. Aqueous humor can thus be delivered to the suprachoroidal space where it can be absorbed, and additional reduction in pressure within the eye can be achieved.

The drug delivery implant can be made from any biological inert and biocompatible materials having the desired characteristics. The elongate body of the implant can in some embodiments be substantially rigid or may be substantially resilient and semi-rigid. Further, in one embodiment the exterior surface of the elongate implant body can be non-porous. Various medically suitable acrylics and other plastics are considered appropriate. The finish of the device preferably meets the standard for ophthalmic devices and does not irritate surrounding tissue. In one embodiment, the device may be made by conventional liquid injection molding or transfer molding process.

Figure 13A:
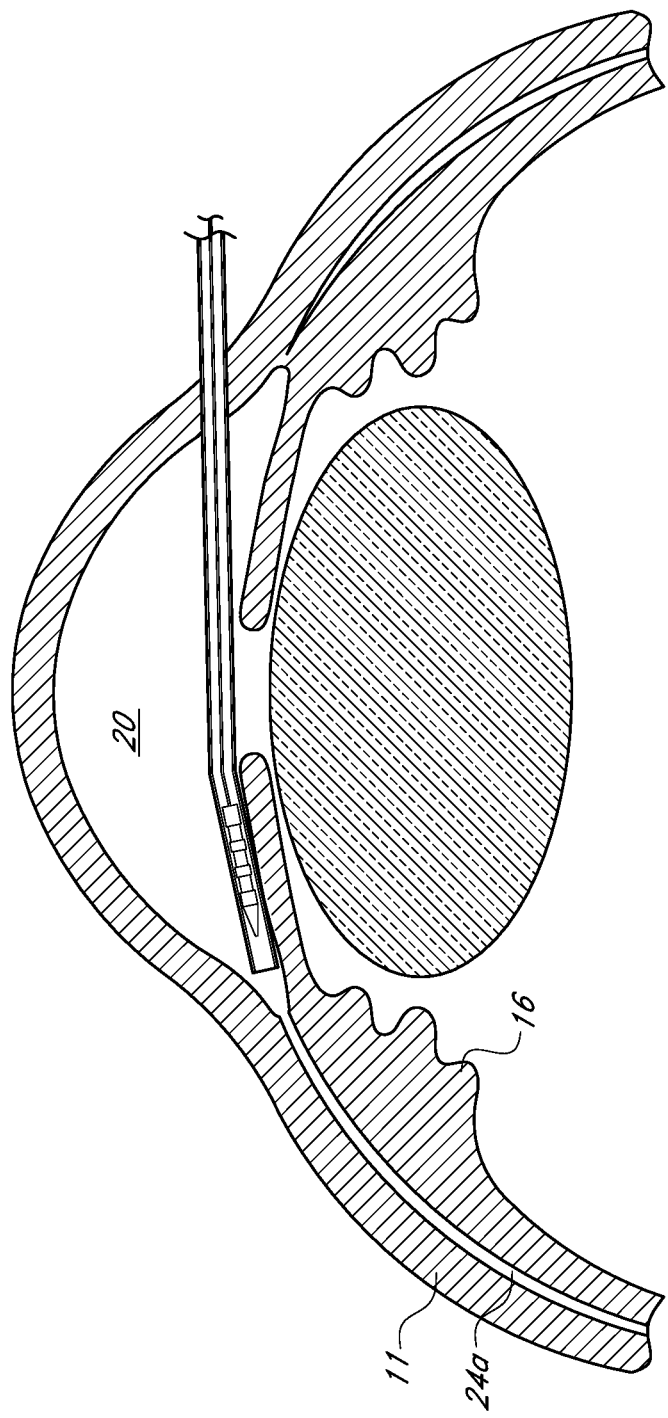
FIG. 13A illustrates a schematic cross-sectional view of an eye with a delivery device containing an implant being advanced across the anterior chamber.

In some embodiments it is desirable to deliver the drug delivery implant ab interno across the eye, through a small incision at or near the limbus (FIG. 13*a*). The overall geometry of the system makes it advantageous that the delivery instrument incorporates a distal curvature, or a distal angle. In the former case, the drug delivery implant can be flexible to facilitate delivery along the curvature or can be more loosely held to move easily along an accurate path. In the latter case, the shunt can be relatively rigid. The delivery instrument can incorporate an implant advancement element (e.g. pusher) that is flexible enough to pass through the distal angle.

Figure 13B:
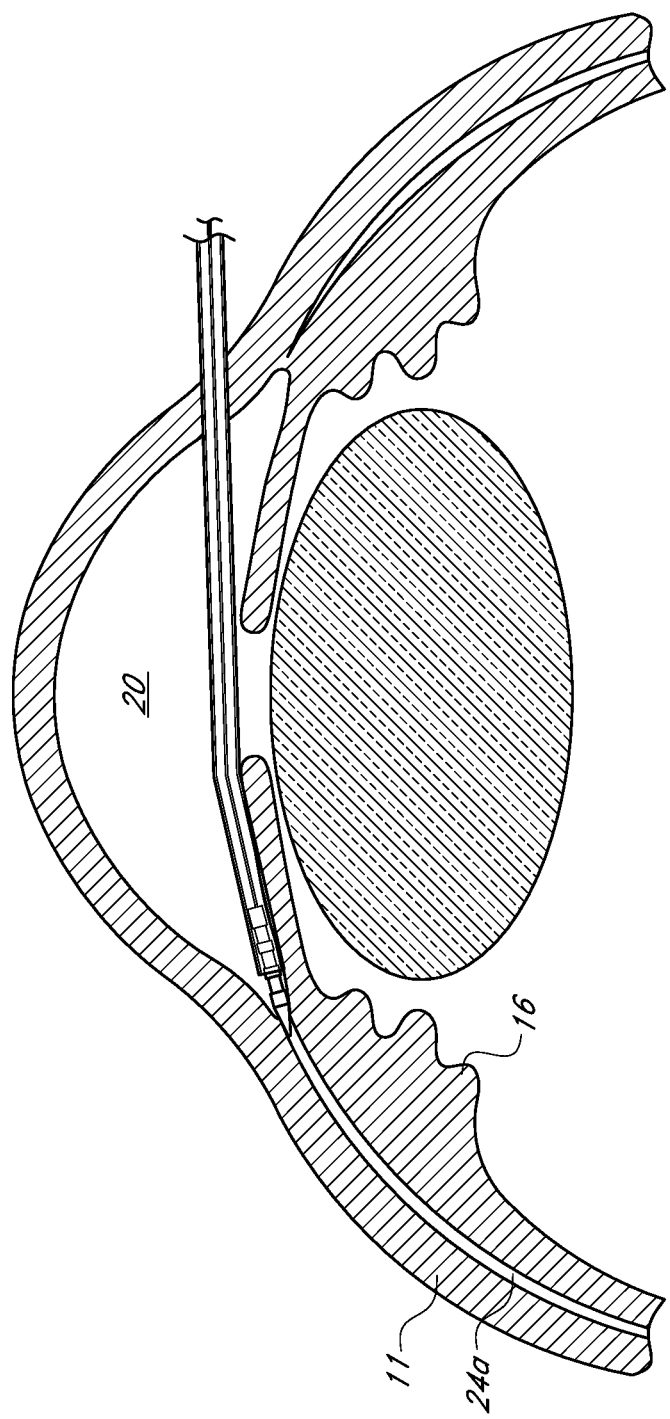
FIG. 13B illustrates a schematic cross-sectional view of an eye with a delivery device being advanced adjacent the anterior chamber angle.
Figure 13C:
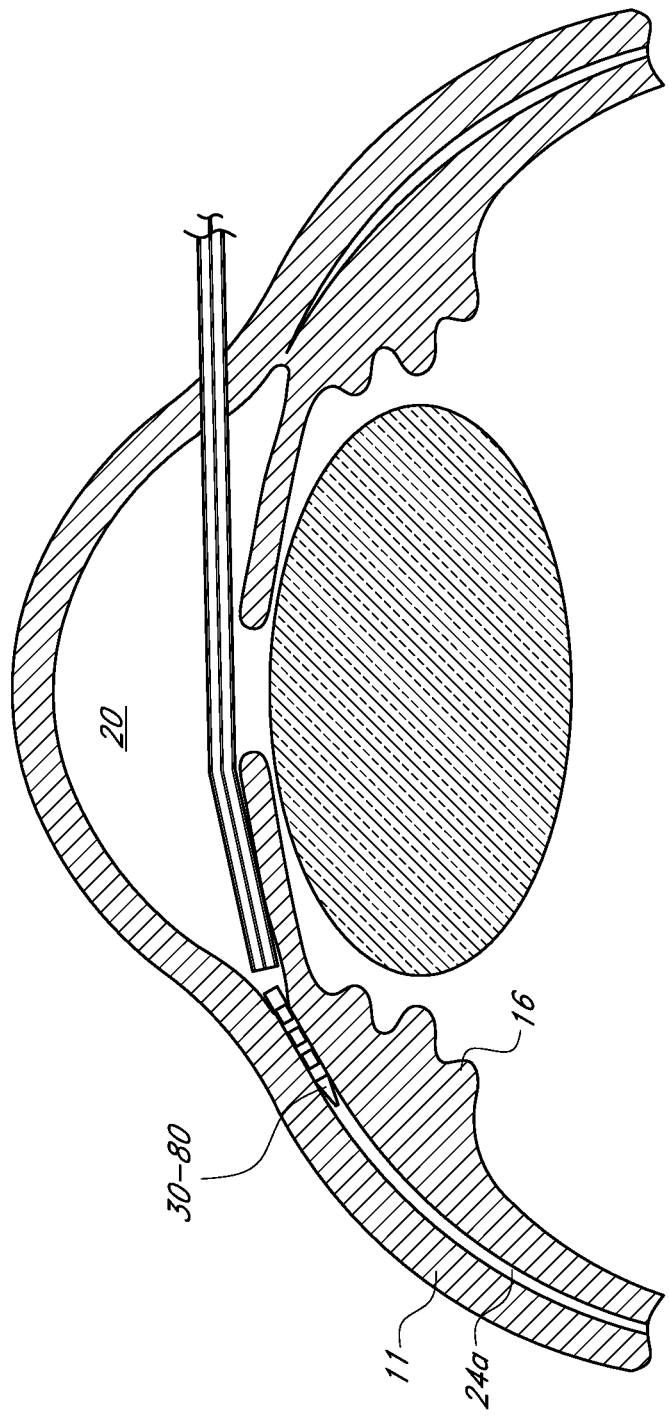
FIG. 13C illustrates a schematic cross-section view of an eye with a delivery device implanting an implant that extends between the anterior chamber and the uveoscleral outflow pathway.

In some embodiments, the implant and delivery instrument can be advanced together through the anterior chamber 20 from an incision at or near the limbus 21, across the iris 13, and through the ciliary muscle attachment until the drug delivery implant outlet portion is located in the uveoscleral outflow pathway 24*a* (e.g. exposed to the suprachoroidal space 24 defined between the sclera 11 and the choroid 12), as shown in FIG. 1. FIG. 13B illustrates, a transocular implantation approach can be used with the delivery instrument inserted well above the limbus 21. The incision, however, can be more posterior and closer to the limbus 21. In other embodiments, the operator can then simultaneously push on a pusher device while pulling back on the delivery instrument, such that the drug delivery implant outlet portion maintains its location in the uveoscleral outflow pathway. The implant can be released from the delivery instrument, and the delivery instrument retracted proximally, as illustrated in FIG. 13C. The delivery instrument then can be withdrawn from the anterior chamber through the incision.

Figure 14:
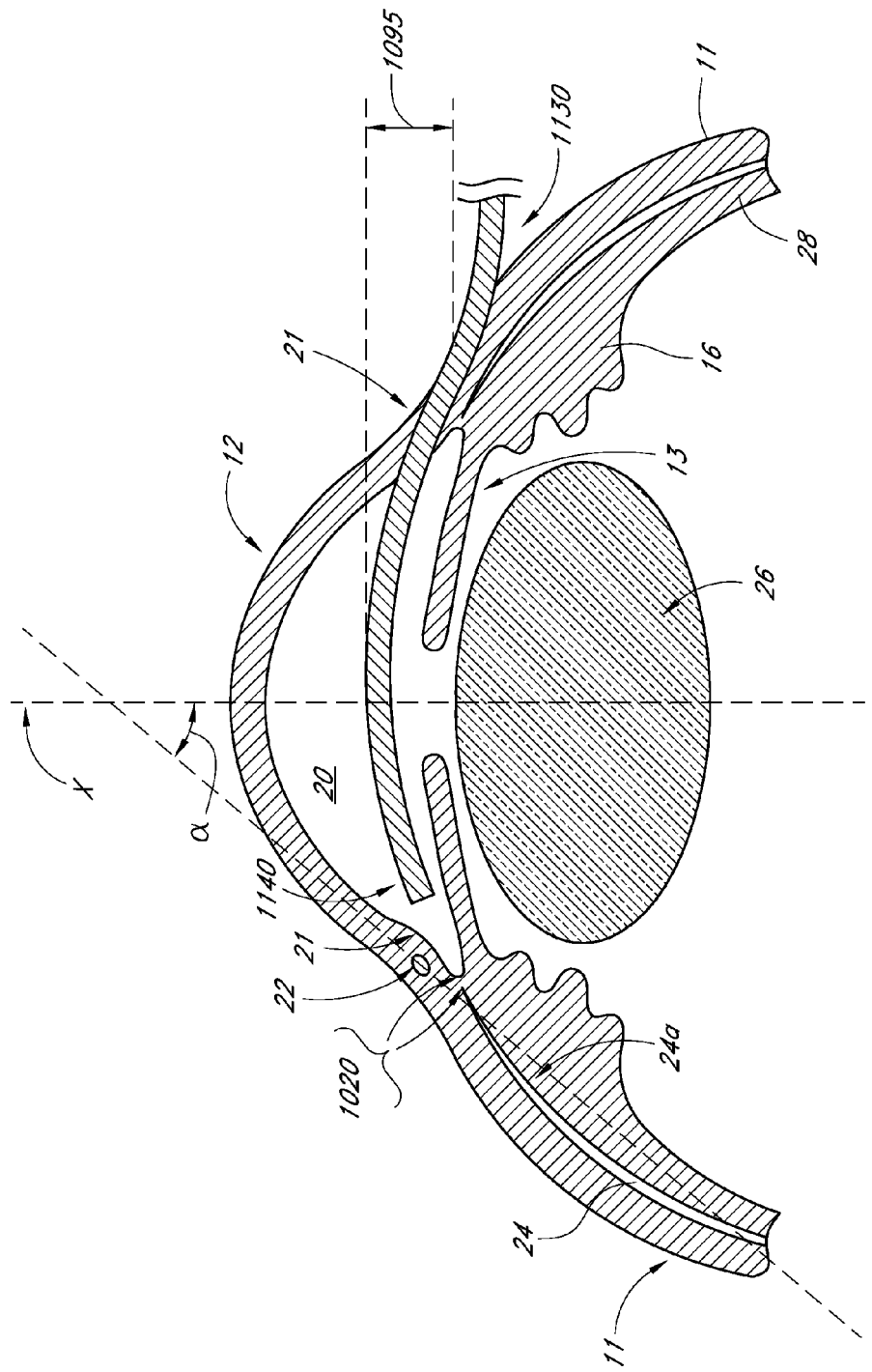
FIG. 14 illustrates a schematic cross-sectional view of an eye with another delivery device being advanced across the anterior chamber for use in delivering an implant into ocular tissue.

FIG. 14 shows a meridional section of the anterior segment of the human eye and schematically illustrates another embodiment of a delivery instrument 1130 that can be used with embodiments of drug delivery implants described herein. In FIG. 14, arrows 1020 show the fibrous attachment zone of the ciliary muscle 16 to the sclera 11. The ciliary muscle 16 is part of the choroid 28. The suprachoroidal space 24 is the interface between the choroid 28 and the sclera 11. Other structures in the eye include the lens 26, the cornea 12, the anterior chamber 20, the iris 13, and Schlemm's canal 22.

In some embodiments, it is desirable to implant a drug delivery implant through the fibrous attachment zone, thus connecting the anterior chamber 20 to the uveoscleral outflow pathway 24*a*, in order to reduce the intraocular pressure in glaucomatous patients. In some embodiments, it is desirable to deliver the drug delivery implant with a device that traverses the eye internally (ab interno), through a small incision in the limbus 21.

The delivery instrument/implant assembly can be passed between the iris 13 and the cornea 12 to reach the iridocorneal angle. Therefore, the height of the delivery instrument/shunt assembly (dimension 1095 in FIG. 14) preferably is less than about 3 mm, and more preferably less than 2 mm.

The suprachoroidal space 24 between the choroid 28 and the sclera 11 generally forms an angle $\alpha$ of about 55° with the optical axis X of the eye. This angle $\alpha$, in addition to the height requirement described in the preceding paragraph, are features to consider in the geometrical design of the delivery instrument/implant assembly.

Figure 15:
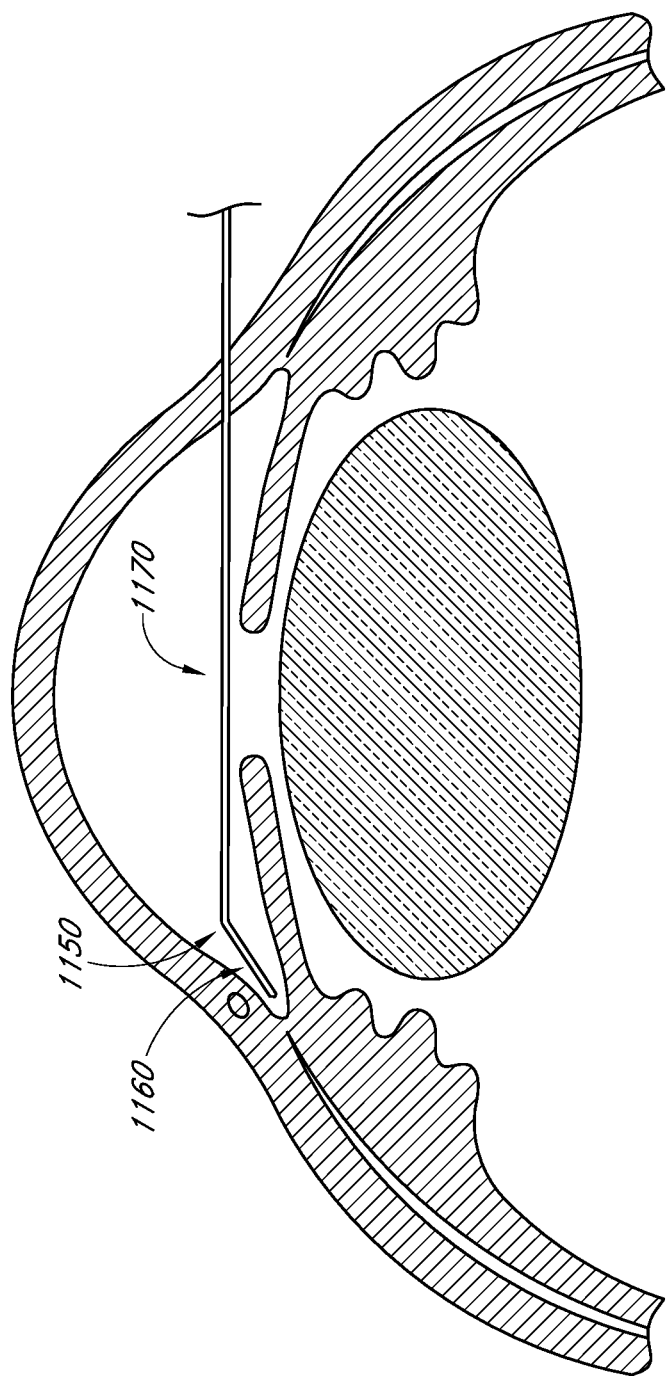
FIG. 15 illustrates a schematic cross-sectional view of an eye with another delivery device being advanced across the anterior chamber for use in delivering an implant into ocular tissue.

The overall geometry of the drug delivery implant system makes it advantageous that the delivery instrument 1130 incorporates a distal curvature 1140, as shown in FIG. 14, or a distal angle 1150, as shown in FIG. 15. The distal curvature (FIG. 14) is expected to pass more smoothly through the corneal or scleral incision at the limbus 21. However, in this embodiment, the drug delivery implant can be curved or flexible. Alternatively, in the design of FIG. 15, the drug delivery implant can be mounted on the straight segment of the delivery instrument, distal of the "elbow" or angle 1150. In this case, the drug delivery implant can be straight and relatively inflexible, and the delivery instrument can incorporate a delivery mechanism that is flexible enough to advance through the angle. In some embodiments, the drug delivery implant can be a rigid tube, provided that the implant is no longer than the length of the distal segment 1160.

The distal curvature 1140 of delivery instrument 1130 may be characterized as a radius of between about 10 to 30 mm, and preferably about 20 mm. The distal angle of the delivery instrument depicted in FIG. 15 may be characterized as between about 90 to 170 degrees relative to an axis of the proximal segment 1170 of the delivery instrument, and preferably about 145 degrees. The angle incorporates a small radius of curvature at the "elbow" so as to make a smooth transition from the proximal segment 1170 of the delivery instrument to the distal segment 1160. The length of the distal segment 1160 may be approximately 0.5 to 7 mm, and preferably about 2 to 3 mm.

In some embodiments, a viscoelastic can be injected into the suprachoroidal space to create a chamber or pocket between the choroid and sclera which can be accessed by a drug delivery implant. Such a pocket could expose more of the choroidal and scleral tissue area, and increase uveoscleral outflow in embodiments where the drug delivery implant includes a shunt, causing a lower intraocular pressure (TOP). In some embodiments, the viscoelastic material can be injected with a 25 or 27G cannula, for example, through an incision in the ciliary muscle attachment or through the sclera (e.g. from outside the eye). The viscoelastic material can also be injected through the shunt itself either before, during or after implantation is completed.

In some embodiments, a hyperosmotic agent can be injected into the suprachoroidal space. Such an injection can delay IOP reduction. Thus, hypotony can be avoided in the acute postoperative period by temporarily reducing choroidal absorption. The hyperosmotic agent can be, for example glucose, albumin, HYPAQUE™ medium, glycerol, or poly (ethylene glycol). The hyperosmotic agent can breakdown or wash out as the patient heals, resulting in a stable, acceptably low IOP, and avoiding transient hypotony.

Variations

In some embodiments, the drug delivery implant can facilitate delivery of a therapeutic agent. The therapeutic agent can be, for example, heparin, TGF-beta, an intraocular pressure-lowering drug, and an anti-proliferative agent. In some embodiments, the therapeutic agent is introduced concurrently with the drug delivery implant. The therapeutic agent can be part of the implant itself. For example, the therapeutic agent can be embedded in the material of the implant, or coat at least a portion of the implant. The therapeutic agent may be present on various portions of the implant. For example, the therapeutic agent may be present on the distal end of the implant and/or the proximal end of the implant. The implant can include combination of therapeutic agents. The different therapeutic agents can be separated or combined. One kind of therapeutic agent can be present at the proximal end of the drug delivery implant, and a different kind of therapeutic agent can be present at the distal end of the drug delivery implant. For example, an anti-proliferative agent may be present at the distal end of the implant to prevent growth, and a growth-promoting agent may be applied to the proximal end of the implant to promote growth. In some embodiments, the therapeutic agent is delivered through the implant to the desired location in the eye, such as the uveoscleral outflow pathway.

If desired, more than one drug delivery implant of the same or different type may be implanted. For example, the drug delivery implants disclosed herein may be used in combination with trabecular bypass shunts, such as those disclosed in U.S. Patent Publication 2004/0050392, and those described in U.S. Patent Publication 2005/0271704, filed Mar. 18, 2005, the entirety of which is incorporated herein by reference and made a part of this specification and disclosure. Such shunts may themselves include a therapeutic agent compounded with a biodegradable polymer such as PLGA, as discussed above. Additionally, implantation may be performed in combination with other surgical procedures, such as cataract surgery. In one embodiment, all or a portion of the drug delivery implant may be coated, e.g. with heparin, preferably in the flow path, to reduce blood thrombosis or tissue restenosis.

While certain embodiments of the disclosure have been described, these embodiments have been presented by way of example only, and are not intended to limit the scope of the disclosure. Indeed, the novel methods, systems, and devices described herein may be embodied in a variety of other forms. For example, embodiments of one illustrated or described shunt can be combined with embodiments of another illustrated or described shunt. Moreover, the shunts described above can be utilized for other purposes. For example, the shunts can be used to drain fluid from the anterior chamber to other locations of the eye or outside the eye. Furthermore, various omissions, substitutions and changes in the form of the methods, systems, and devices described herein may be made without departing from the spirit of the disclosure.

What is claimed is:

1. An intraocular implant comprising:
    a generally elongated body having a proximal end, a distal end, a long axis and being configured for implantation in eye tissue such that the proximal end of the implant is in fluid communication with an anterior chamber of an eye and the distal end is in fluid communication with a suprachoroidal space of the eye;
    a first recess formed in the body and extending from one end of the body towards the other end and generally along a first axis parallel to the long axis;
    only a single lumen within the body and extending from the proximal to the distal end generally along a second axis parallel to the long axis, the lumen configured to allow flow therethrough,
    wherein the first and the second axes are offset from a central plane extending from the proximal end to the distal end of the elongated body and bisecting the elongated body along a central longitudinal axis of the elongated body, and wherein the first axis is positioned offset from the central longitudinal axis on a first side of the central plane and the second axis is positioned offset from the central longitudinal axis on a second side of the central plane; and
    a therapeutic agent disposed in the recess in a sufficient quantity to treat the eye over a desired period of time.

2. The implant of claim 1, wherein the implant comprises a second recess formed in the body and extending from one end of the body towards the other end and generally along the first axis.

3. The implant of claim 2, wherein at least a portion of the therapeutic agent is in fluid communication with the lumen.

4. The implant of claim 1, further comprising therapeutic agent disposed on an outer surface of the elongated body, said therapeutic agent configured to contact ocular tissue following implantation of the drug delivery implant.

5. The implant of claim 1, wherein the therapeutic agent is compounded with a biodegradable polymer adapted to provide the desired rate of release.

6. An implant for treating glaucoma, comprising:
a body having a proximal end and a distal end, the body configured for implantation in an eye between an anterior chamber and suprachoroidal space of the eye, the body including a therapeutic agent disposed in a first recess extending generally along a first axis, said body having only a single lumen extending between an inlet portion and an outlet portion of the body along a second axis, said inlet portion configured to transport aqueous fluid from the anterior chamber of the eye to the outlet portion, where the outlet portion is disposed in the suprachoroidal space of the eye, said outlet portion having an outflow opening;
wherein the first and the second axes are offset from a central plane extending from the proximal end to the distal end of the elongated body and bisecting the elongated body along a central longitudinal axis of the body, and wherein the first axis is positioned offset from the central longitudinal axis on a first side of the central plane and the second axis is positioned offset from the central longitudinal axis on a second side of the central plane.

7. The implant of claim 6, wherein the therapeutic agent is in fluid communication with the lumen such that said aqueous fluid contact the therapeutic agent as it flows through the lumen.

8. The implant of claim 6, wherein the therapeutic agent is disposed on an outer surface of the body and is configured to contact ocular tissue following implantation of the implant.

9. A system for treating glaucoma comprising:
a plurality of implants having a proximal end and a distal end, the plurality of implants configured for implantation into eye tissue, one or more of the implants comprising one or more drug delivery portion extending generally along a first axis which, following implantation at an implantation site in the eye, delivers one or more therapeutic agent to one or more of the anterior chamber and the suprachoroidal space of the eye;
one or more of the implants comprises only a single lumen extending generally along a second axis offset from the first axis;
wherein the first and second axes are offset from a central plane extending from the proximal end to the distal end of the plurality of implants and bisecting the plurality of implants along a central longitudinal axis of a body of one or more implants, and wherein the first axis is positioned offset from the central longitudinal axis on a first side of the central plane and the second axis is positioned offset from the central longitudinal axis on a second side of the central plane; and
an instrument having a chamber in which the implants are loaded for serial delivery into eye tissue;
wherein at least a first implant of the plurality of implants is configured to extend generally alongside a second implant of said plurality of implants.

10. The system of claim 9, wherein at least one of the one or more drug delivery portion comprises at least one of the one or more therapeutic agent compounded with a biodegradable PLGA copolymer, wherein the lactic acid to glycolic acid ratio and/or average molecular weight of the PLGA copolymer is selected to achieve a desired delivery rate of the therapeutic agent over time.

11. A system for treating an ocular disorder in a patient, comprising:
the drug delivery implant of claim 1, following implantation at an implantation site in the eye, delivers said therapeutic agent to one or more of the anterior chamber and the uveoscleral outflow pathway of an eye; and
a delivery instrument releasably coupleable to the drug delivery implant for implanting the drug delivery implant, said instrument configured to deliver the implant through an insertion site in the sclera to a location in the suprachoroidal space proximate the anterior chamber, said instrument comprising a plurality of members longitudinally moveable relative to each other.

12. The system of claim 11, wherein the drug delivery implant is configured to deliver one or more therapeutic agent to the suprachoroidal space of the uveoscleral outflow pathway.

13. The system of claim 11, wherein the instrument has a sufficiently small cross section such that the insertion site self seals without suturing upon withdrawal of the instrument from the eye.

14. The system of claim 11, wherein the implant comprises a lumen extending configured to allow fluid communication between the anterior chamber of the eye and the uveoscleral outflow pathway following implantation of the implant.

15. The system of claim 11, wherein at least one of the one or more drug delivery portion comprises at least one of the one or more therapeutic agent compounded with a biodegradable PLGA copolymer, wherein the lactic acid to glycolic acid ratio and/or average molecular weight of the PLGA copolymer is selected to achieve a desired delivery rate of the therapeutic agent over time.

16. A method for reducing intraocular pressure in an eye of a mammal, comprising:
introducing the ocular implant of claim 1 through an incision in ocular tissue;
advancing the implant to an implantation site in a uveoscleral outflow pathway of the eye such that the proximal end of the implant is in communication with the anterior chamber of the eye and the distal end of the implant is in communication with the suprachoroidal space of the eye.

17. The method of claim 16, wherein introducing the implant comprises introducing the implant through an incision in the sclera of the eye made posteriorly of the limbus of the eye, the ocular implant advanced anteriorly into said position in the uveoscleral path.

18. The method of claim 16, wherein introducing the implant comprises introducing the implant across the anterior chamber of the eye through an incision at or near a limbus of the eye opposite from the implantation site, advancing the implant across the anterior chamber and posteriorly along the uveoscleral outflow pathway into said implantation site such that the distal end of the implant is located in the suprachoroidal space and the proximal end of the implant is located in the anterior chamber.

19. The method of claim 16, further comprising conducting aqueous humor through the implant between the proximal and distal ends of the implant.

20. The implant of claim 1, wherein the therapeutic agent is selected from the group consisting of timolol, atenolol, propranolol, metipranolol, betaxolol, carteolol, levobetaxolol, and levobunolol.

21. The implant of claim 1, further comprising a second recess, wherein the first recess is formed in one end of the body, and the second recess is formed in the other end of the body.

22. The implant of claim 1, wherein the first recess comprises an inner wall surrounded by a first material of the elongated body, and wherein the inner lumen wall is surrounded by the first material on a first side and a second side of the inner lumen.

23. The implant of claim 6, further comprising a second recess, wherein the first recess is formed in one end of the body, and the second recess is formed in the other end of the body.

\* \* \* \* \*